United States Patent [19]

Bevan et al.

[11] Patent Number: 5,078,998
[45] Date of Patent: Jan. 7, 1992

[54] HYBRID LIGAND DIRECTED TO ACTIVATION OF CYTOTOXIC EFFECTOR T LYMPHOCYTES AND TARGET ASSOCIATED ANTIGEN

[76] Inventors: Michael J. Bevan, 1579 Gascony Rd., Leucadia, Calif. 92024; Uwe D. Staerz, 4644 Fargo Ave., San Diego, Calif. 92117

[21] Appl. No.: 762,048

[22] Filed: Aug. 2, 1985

[51] Int. Cl.[5] .................. A61K 39/44; C07K 15/06
[52] U.S. Cl. .................................. 424/85.8; 530/391
[58] Field of Search .................... 530/387–389, 530/391; 424/85.93, 85.8, 85.91; 435/2, 29, 259; 935/106–108; 436/813, 819; 514/2, 8

[56] References Cited

PUBLICATIONS

Marty Ie., Immunology Today, vol. 5, No. 9, (254–255, (1984).

Staerz, V. D. et al., Nature, 314:628–631, (Apr. 18, 1985).

Staerz, V. D. et al., Journal of Immunology, 134(6): 3994–4000, (Jun. 1985).

Karpovsky, B. et al., J Exper. Med., 160:1686–1701, (12–1984).

"Use of Anti-Receptor Antibodies to Focus T-Cell Activity", published in *Immunology Today*, 7:241–245, (1986), co-authored by Drs. Bevan and Staerz.

Primary Examiner—Margaret Moskow
Assistant Examiner—Lila Feisee

[57] ABSTRACT

A hybrid ligand molecular composed of an antibody combining site that binds to a T cell receptor complex structure and is capable of activating cytotoxic T lymphocytes linked to a target cell-specific antibody is disclosed. This ligand molecule can bind to an antigen on the surface of a target cell and to cytotoxic effector T lymphocyte cell receptor complex structures. A composition and a method for killing tumor cells with the hybrid ligand molecule of this invention are provided.

13 Claims, 9 Drawing Sheets

$^{125}$I-CTL CLONE, G4

| NMS | F9 | C1 | C3 | | NMS | F9 | C1 | C3 |
|---|---|---|---|---|---|---|---|---|
| | | ▬ | ▬ | —200— | | | | |
| | | | | —96— | | | | |
| | ● | | | —69— | | | | |
| | | | | —46— | | | | |
| | | | | —31— | | | | |

| 1 | 2 | 3 | 4 | | 5 | 6 | 7 | 8 |

Non-Reduced        Reduced

FIG. 2

HYBRID LIGAND DIRECTED TO ACTIVATION OF CYTOTOXIC EFFECTOR T LYMPHOCYTES AND TARGET ASSOCIATED ANTIGEN

This invention was made with the support of the United States Government, and the United States Government has certain rights in the invention.

TECHNICAL FIELD

The present invention relates to ligand molecules, and, more particularly to ligand molecules comprising a cytotoxic effector T lymphocyte-activating agent linked to a target cell-associated antibody combining site.

BACKGROUND OF THE INVENTION

Two recent approaches have provided insights into the possible mechanisms of antigen recognition by different subsets of T lymphocytes, as well as into the structures involved in the first step of a series of events leading towards the induction of T cell activation.

Reports that monoclonal antibodies could interfere with the activation and function of T cells have directed interest to a complex system of molecules on the surface of this subpopulation of lymphocytes. Clonotypic antibodies capable of both inducing and inhibiting functions of human and murine cytotoxic T lymphocytes (CTL), Meuer et al., *J. Exp. Med.*, 157, 705 (1983), Reinherz et al., *Proc. Natl. Acad. Sci. (USA)*, 80, 4104 (1983), Meuer et al., *J. Exp. Med.*, 158, 388 (1983), Staerz et al., *Proc. Natl. Acad. Sci. (USA)*, 81, 1799 (1984), and Lancki et al., *J. Exp. Med.*, 157, 821 (1983), and T helper lymphocytes, Haskins et al., *J. Exp. Med.*, 157, 1149 (1983), Kappler et al., *Cell*, 34, 727 (1983), Samelson et al., *Proc. Natl. Acad. Sci. (USA)*, 80, 6972 (1983), and Kaye et al., *J. Exp. Med.*, 158, 836 (1983), provided information that indicated that a disulfide-linked heterodimer, first reported by Allison et al., *J. Immunol.*, 129, 2293 (1982), was the most likely candidate for the so-called T cell antigen receptor. In reports to date, clone-specific monoclonal antibodies precipitated a surface protein of 80,000–90,000 daltons that separated into two chains of about 42,000 daltons each upon reduction.

In a second reported approach, the search for T cell-specific cDNA provided additional genetic and structural information for at least one chain of the clonotypic heterodimer, indicating its close resemblance to the proteins of the major histocompatibility complex and to the immunoglobulin chains, Hedrick et al., *Nature*, 308, 149 (1984), Yanagi et al., *Nature*, 308, 145 (1984), and Saito et al., *Nature*, 309, 757 (1984). In particular, the gene for the so-called beta chain was organized in a similar manner as were immunoglobulin genes including a set of variable genes, D segments, joining segments and genes for the constant region of the T cell antigen receptor, Hedrick et al., *Nature*, 308, 153 (1984), Malissen et al., *Cell*, 37, 1101 (1984), Chien et al., *Nature*, 309, 322 (1984), Gascoigne et al., *Nature*, 310, 387 (1984), and Kavaler et al., *Nature*, 310, 421 (1984).

The use of clone-specific (i.e., anti-idiotypic) monoclonal antibodies to perform a crude purification of the T cell receptor for the production of "second generation" antibodies that react with subsets of T cells has also been reported. Both a rabbit antiserum against the murine T cell antigen receptor of the T helper subset, McIntyre et al., *Cell*, 34, 739 (1983), and a rat monoclonal antibody KJ16-133 against a subset of T lymphocytes, Haskins et al., *J. Exp. Med.*, 160, 452 (1984), have been described. KJ16-133 reportedly bound to an allotypic structure on about 20 percent of peripheral T cells in BALB mice and most other strains of laboratory mice. This determinant was absent in a few strains. The KJ16-133 antibody was reported to react with receptors on mature and immature thymocytes, and on both L3T4+ and Lyt2+ peripheral T cells, Roehm et al., *Cell*, 38, 577 (1984).

Hybrid antibodies consisting of two different antibody fragments having two different specificities have been reported. Milstein et al., *Immunol. Today*, 5, 299 (1984), Nisonoff et al., *Arch. Biochem. Biophys.*, 93, 460 (1961), Milstein et al., *Nature*, 305, 537 (1983), Kohler et al., *Nature*, 256, 495 (1975), Hammerling et al., *J. Exp. Med.*, 128, 1461 (1968), Paulus, U.S. Pat. No. 4,444,878, and Ehrlich et al., U.S. Pat. No. 4,355,023. Target-specific effector cells using hetero-cross-linked aggregates containing anti-target cell and anti-$F_c$ portion of IgG receptor antibodies were reported in Karpovsky et al., *J. Exp. Med.*, 160, 1686 (1984).

However, heretofore, no hybrid antibodies have been reported having the T cell antigen receptor specificity in at least one of the antibody combining sites of the hybrid antibody, nor having the capability of inducing cytotoxic effector T lymphocytes that lyse the target cell. Such hybrid antibodies have also not been suggested.

SUMMARY OF THE INVENTION

The present invention contemplates a ligand molecule comprising a cytotoxic effector T lymphocyte-activating agent linked to a target cell-associated antibody combining site. The cytotoxic effector T lymphocyte-activating agent is preferably an antibody combining site directed to a T cell receptor complex structure, and the target cell-associated antibody combining site is directed to a target cell-associated antigen.

In one aspect of the present invention, the ligand molecule of the invention is a hybrid ligand comprising a plurality of different linked antibody combining sites. One of the antibody combining sites binds to a T cell receptor complex structure, and a second of the combining sites binds to a target cell-associated antigen.

In another aspect of the invention, a composition including an effective amount of a hybrid ligand of the invention dispersed in a physiologically tolerable diluent. The composition, when contacted in an effective amount in vitro with target cells in the presence of an exogenously supplied source of cytotoxic effector T lymphocytes, induces lysis of the target cells by the cytotoxic effector T lymphocytes.

In yet another aspect of the invention the composition includes a hybrid ligand of the invention, dispersed in a physiologically tolerable diluent, comprising one antibody combining site that binds to a T cell receptor complex structure, and is thus directed to a T cell antigen receptor on the surface of T lymphocytes, linked to a second antibody combining site that binds to a target cell-associated antigen. The antibody combining site binding to a T cell receptor complex structure can alternatively be directed to a T3 complex or the major histocompatibility complex on the surface of T lymphocytes. The antibody combining site that binds to a target cell-associated antigen can be directed to a tumor cell-associated antigen or to a viral protein or oncogene expressed on the surface of the target cell.

In a further aspect of the present invention, a composition for killing tumor cells is contemplated. The composition includes a unit dose of the before-described hybrid ligand molecule of the invention dispersed in a physiologically tolerable diluent and, when introduced in an effective amount into the blood stream of an animal host, induces lysis of the tumor cells by cytotoxic effector T lymphocytes.

In a still further aspect of the present invention, a method of killing tumor cells is contemplated. The method includes (a) providing the before-described composition that induces lysis of tumor cells by cytotoxic effector T lymphocytes that react with cells bearing a tumor cell-associated antigen; (b) contacting tumor cells that bear the antigen with an effective amount of the composition in the presence of a source of cytotoxic effector T lymphocytes whose production is activated by the first antibody combining site of the composition; and (c) maintaining the contact for a time period sufficient (i) for the second antibody combining site of the composition to bind to the tumor cell-associated antigen, and (ii) for the first antibody combining site to activate cytotoxic effector T lymphocytes that cytotoxically react with the antigen-bearing tumor cells. The contacting can occur in an in vitro tumor cell culture when the source of cytotoxic effector T lymphocytes is supplied exogenously to the cell culture. The composition can alternatively be provided in vivo to the blood stream of a host animal having a tumor bearing the above antigen and whose immune system supplies the source of stimulable cytotoxic effector T lymphocytes. Steps (b) and (c) of the method can be periodically repeated until substantially all of the tumor cells have been killed.

The present invention provides several benefits and advantages.

One benefit of the present invention is that the compositions of the invention can be utilized to focus T cell activity at a chosen target antigen site. Until the present invention, it was not possible to utilize T cell immunity in the same way as antibody combining sites may be utilized. While it was possible to make monoclonal effector T cells, these cells recognized antigen only in conjunction with the major histocompatibility (MHC) antigens with which they were generated with the expected MHC restriction of T cell function.

Another benefit of the present invention is that the method of killing tumor cells of the invention makes it possible to induce T cell activity from a host's own T cell pool by activating cytotoxic effector T lymphocytes and directing them to a target cell-associated antigen using the composition of the invention. In this manner, problems associated with MHC restriction of T cell recognition and of rejection are circumvented.

One of the advantages of the present invention is that a composition of the invention can be utilized in the therapy of certain diseases in situations in which it would be desirable to direct a strong T cell response to a particular target antigen, such as a tumor cell-associated antigen.

Other benefits and advantages of the present invention will become readily apparent to those skilled in the art from the following detailed description of the invention, the drawings and the appended claims.

BRIEF DESCRIPTION OF THE DRAWINGS

In drawings forming a portion of the disclosure of this invention:

FIG. 2 is a photograph of an autoradiograph showing the reaction of antisera with the T cell antigen receptors of T lymphocytes in BALB.B mice. The antisera C1 and C3 did not immunoprecipitate the disulfide-linked heterodimer from the BALB-B derived, cloned cytotoxic T cell line, G4. Surface-radioiodinated G4 cells were lysed and immunoprecipitated by normal C57L serum (lanes 1 and 5), the clone specific monoclonal antibody (Mab) F9A7.3 (lanes 2 and 6), the immune sera C1 (lanes 3 and 7) and C3 (lanes 4 and 8). The isolated material was analyzed under non-reducing (lanes 1 through 4) and reducing (lanes 5 through 8) conditions.

DETAIELD DESCRIPTION OF THE INVENTION

Figure 1:
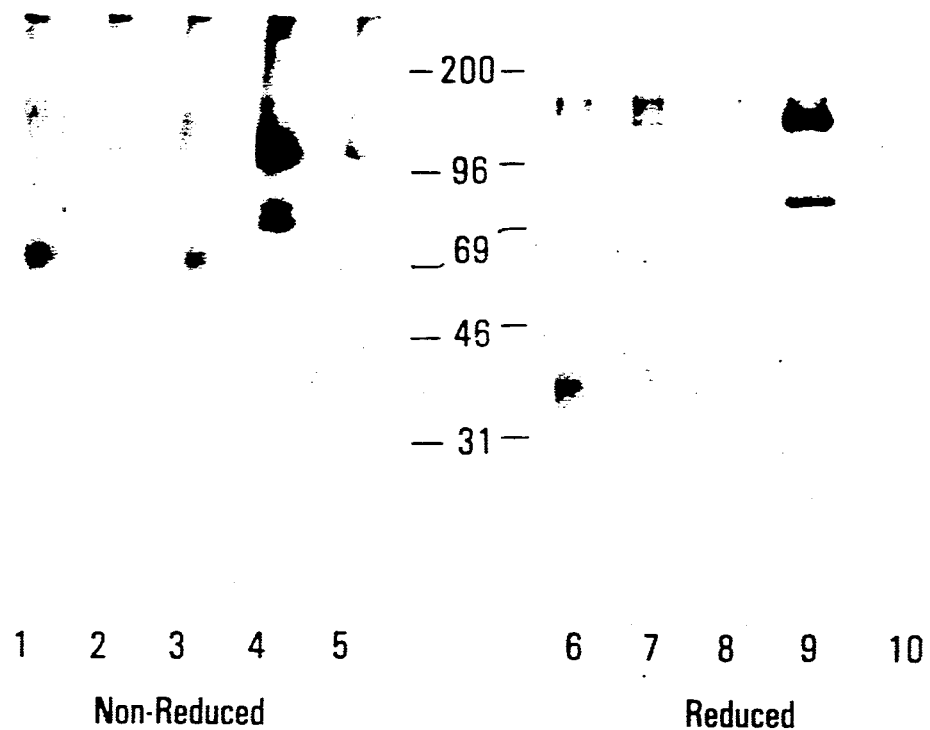
FIG. 1 is a photograph of an autoradiograph showing the results of immunoprecipitations with antisera from five C57L/J mice immunized with BALB.B peripheral T cells. Material isolated from detergent lysates of surface radioiodinated BALB.B T cells by immunoprecipitation with antisera C1 (lanes 1 and 6), C2 (lanes 2 and 7), C3 (lanes 3 and 8), C4 (lanes 4 and 9), and C5 (lanes 5 and 10) was analyzed by sodium dodecyl sulfate-polyacrylamide gel electrophoresis (SDS-PAGE) under non-reducing conditions (lanes 1 through 5) and reducing conditions (lanes 6 through 10). All lanes show precipitates from about 1x106 cells. Further procedural details may be found in Section III A.6, hereinafter.

The present invention is directed to a ligand molecule, compositions including the ligand molecule and to methods of preparing and using same. The ligand molecule comprises a cytotoxic effector T lymphocyte activating agent linked to a target cell-associated antibody combining site.

I. General Discussion

A. Definitions

The term "antibody combining site" as used herein is meant to indicate a biologically active molecule that binds to an antigen. The antibody combining sites of the present invention are whole antibodies, substantially intact antibodies or idiotype-containing polypeptide portions of antibodies.

Biological activity of an antibody combining site molecule is evidenced by the binding of the combining site to its antigen upon their admixture in an aqueous medium, at least at physiological pH values and ionic strengths. Preferably, the combining sites also bind to the antigen within a pH value range of about 5 to about 9, and at ionic strengths such as that of distilled water to that of about one molar sodium chloride.

Idiotype-containing polypeptide portions of antibodies are those portions of antibody molecules that contain the idiotype and bind to the antigen, and include the Fab, F(ab')$_2$ and Fab' portions of the antibodies. Fab, F(ab')$_2$ and Fab' portions of antibodies are well known in the art, and are prepared by the reaction of papain, pepsin, and pepsin followed by reduction and alkylation as discussed hereinafter, respectively, on whole or substantially intact antibodies by methods that are well known. See for example, U.S. Pat. No. 4,342,566 to Theofilopolous and Dixon.

Each of the antibody combining sites useful in the present invention is preferably monoclonal and is obtained from a monoclonal antibody. A "monoclonal antibody" (Mab) is an antibody produced by clones of a single cell called a hybridoma that secretes but one kind of antibody molecule. The hybridoma cell is produced by fusion of an antibody-producing cell and a myeloma or other self-perpetuating cell line. Such antibodies were first described by Kohler and Milstein, *Nature*, 256, 495–497 (1975), which description is incorporated herein by reference.

Monoclonal antibodies are typically obtained from supernatants of hybridoma tissue cultures, the preferred method for obtaining the monoclonal antibody combining sites of the present invention, or, alternatively, from ascites fluid obtained from animals into which the hybridoma tissue was introduced. Both methods are described in detail hereinafter.

To form the hybridoma from which the monoclonal antibody is produced, a myeloma cell line is fused with mammalian lymphocytes that secrete antibodies that react with T cell antigen receptor, such as splenocytes from an animal immunized with the T cell antigen receptor. It is preferred that the myeloma cell line be from the same species as the lymphocytes. Therefore, fused hybrids such as mouse-mouse hybrids [Shulman et al., *Nature*, 276, 269 (1978)] or rat-rat hybrids [Galfre et al., *Nature*, 277, 131 (1979)] are typically utilized. However, some rat-mouse hybrids have also been successfully used in forming hybridomas [Goding, "Production of Monoclonal Antibodies by Cell Fusion," in *Antibody as a Tool*, Marchalonis et al. eds., John Wiley & Sons Ltd., p. 273 (1982)].

Suitable myeloma lines for use in the present invention include MPC-11 (ATCC CRL 167), P3×63-Ag8.653 (ATCC CRL 1580), Sp2/0-Ag14 (ATCC CRL 25 1581), P3×63 Ag8U.1 (ATCC CRL 1597), Y3-Ag1.2.3.(deposited at Collection Nationale de Cultures de Microorganisms (CNCM), Paris, France, number I-078) and P3×63Ag8 (ATCC TIB 9).

The words "secrete" and "produce" are often used interchangeably in the art as to cells from which antibody molecules are obtained. Cells that produce antibodies may, however, not secrete those molecules into their environment. The hybridoma cells of interest herein secrete monoclonal antibodies into their environment. Nevertheless, such cells are often referred to herein as "antibody-producing" cells, and their antibodies are referred to as being "produced" in keeping with the phrase utilized in the art.

B. The Invention

The present invention contemplates a ligand molecule alone, ligand molecules dispersed in a physiologically tolerable diluent and methods involving the same.

A ligand molecule of this invention comprises a cytotoxic effector T lymphocyte activating agent linked to a target cell-associated antibody combining site.

In a preferred embodiment of the invention, the ligand molecule is a hybrid ligand comprising a plurality of different linked antibody combining sites, a first of which binds to an antigenic T cell receptor complex structure,,such as a T cell antigen receptor, T3 complex or the major histocompatibility complex on the surface of T lymphocytes. A second ligand antibody combining site of the individual ligand molecules binds to a target cell-associated antigen that is preferably a tumor cell-associated antigen. That antigen can also be a viral protein such as that produced by vescular stomatitis virus or an oncogene product such as those produced by v-sis that encodes residues 139-155 of protein $28^{sis}$ and v-fes that encodes residues 744-759 of protein $p85^{fes}$ and their cellular counterparts such as PDGF and proteins homologous to that produced by v-fes that are expressed on the surface of the target cell.

Thus, a ligand molecule of the present invention is a hybrid or composite that contains at least two antibody combining sites of different binding specificities linked together. The two antibody combining sites must be linked together so that the cytotoxic T lymphocyte can be brought into lytic contact with the target cell. One of the binding sites immunologically binds to an antigen present on the surface of resting, precursor T cells and induces production (differentiation and proliferation) of cytotoxic T lymphocytes from those precursor T cells. The second antibody combining site immunologically binds to an antigen present on the surface of the target cell to be lysed and killed by the cytotoxic T lymphocyte activated by the first antibody combining site.

The illustrative ligand molecules described herein were prepared using antibody combining sites of two different, intact antibodies. It is noted that one or both antibody combining sites of the ligand molecule may be Fab, Fab' or F(ab')$_2$ portions of intact antibodies. The techniques for preparing ligand molecules using idiotype-containing polypeptide portions of antibodies are the same as those where intact antibodies are utilized. It is further noted that the antibody combining sites need not be of monoclonal origin, and that polyclonal antibodies can be used. Ligand molecules prepared from intact antibodies are preferred, particularly when the action of the complement system is desired to assist in the killing of target-bearing cells.

It is particularly preferred that a plurality of the ligand molecules be linked to a matrix when they are used to activate production of cytotoxic T lymphocytes. A particularly preferred matrix is the cross-linked dextran sold under the trademark Sepharose by Pharmacia Fine Chemicals of Piscataway, NJ. Macrophages may also be used as the matrices.

It is noted that the antigens present on T cells binding to which induces or activates production of cytotoxic T lymphocytes is referred to as a T cell receptor. That "receptor" is an antigen for an antibody combining site of this invention and has similarities to antibody combining sites and binds to naturally occurring stimulatory molecules. Because of its antibody combining site-like properties, antibodies raised to the T cell receptor are often referred to in the art and herein as anti-idiotype antibodies.

Exemplary of the cytotoxic T lymphocyte-inducing antibody combining sites useful in a ligand molecule of this invention are those of the monoclonal antibodies denominated herein as Mab F23.1, Mab F23.2, Mab KJ16-133, and Mab F9A7.3. Each of those antibody combining sites immunoreacts with (binds to) a receptor structure of resting T cells, and when bound to or immunoreacted with the T cell receptor structure induces production of cytotoxic T cells (CTL). Additionally, useful cytotoxic T cell-activating antibody combining sites include that produced by the hybridoma ATCC CRL 8001 and denominated OKT3 that is available commercially from Ortho Pharmaceuticals, Inc. of Raritan NJ, and is described in U.S. Pat. No. 4,361,549, which description is incorporated herein by reference, and antibody combining sites directed against the so-called T3 complex of T cells, as are described in van de Rijn et al., Science, 226, 1083 (1984).

As has been reported in Gratama et al., Transplantation, 38, 469 (1984), the use of whole OKT3 monoclonal antibodies has a detrimental effect on T cell function. One mechanism of the action of OKT3 could be a direct blockage of T cell function by modulation of the molecule bearing the T3 antigen. The most likely mechanism of the temporary T cell loss is opsonization by antibody with removal of coated cells by the reticuloendothelial system, rather than complement-dependent cell killing, because OKT3 does not effectively fix human complement. Consequently, to avoid loss of T cell function, the Fc portion of OKT3 is removed prior to use of OKT3 in the present invention. The remaining Fab and F(ab')$_2$ portions of OKT3 are useful in activating cytotoxic T cells.

The second antibody combining site of the ligand molecules of this invention is raised to an antigen on a target cell. The specific antigen used in the illustrative receptor molecules herein is the Thy-1.1 antigen that is bound by Mab 19E12. Exemplary of other, useful antibody combining sites are those of monoclonal antibodies produced by hybridoma cell lines ATCC HB 8341, ATCC HB 8342, ATCC HB 8343, ATCC HB 8344, ATCC HB 8345, ATCC HB 8346, ATCC HB 8347, ATCC HB 8348, and ATCC HB 8349, directed against antigens expressed on the surface of human astrocytoma tumor cells, and CNCM No. I-195 directed against carcinoma tumors.

Antibody combining sites that bind to oncogene translation products (oncoproteins) expressed on cell surfaces are also useful as second antibody combining sites of ligand molecules. Exemplary of such antibody combining sites are those described in Niman et al., Science, 226, 701 (1984) and Niman, Nature, 307, 180 (1984).

Antibody binding sites that immunoreact with viral proteins are also useful herein where the virus is processed on a host cell surface. As noted previously, vesicular stomatitis virus is one such virus.

A composition of this invention includes a unit dose of the above-described ligand molecule dispersed in a physiologically tolerable diluent. Exemplary diluents include distilled or deionized water, phosphate-buffered saline, normal saline and the like.

The term "unit dose" refers to physically discrete units suitable as unitary dosages for animals, each unit containing a predetermined quantity of active material calculated to produce the desired therapeutic effect in association with the required diluent; i.e., carrier or vehicle.

Such a composition, when contacted in an effective amount in vitro with the target cells in the presence of an exogenously supplied source of cytotoxic effector T lymphocytes (CTL), induces lysis of the target cells by the cytotoxic effector T lymphocytes. Similarly, when introduced into the blood stream of an animal host, such a composition induces lysis of target-bearing cells such as tumor cells by production of endogenous effector T lymphocytes.

In yet another embodiment of the invention, a method of killing tumor cells is contemplated. The method includes the steps of (a) providing an above-described composition that induces lysis of a tumor cell by cytotoxic effector T lymphocytes that react with cells that bear a tumor cell-associated antigen; (b) contacting tumor cells that bear the antigen with an effective amount of the composition in the presence of a source of cytotoxic effector T lymphocytes whose production is activated by the first antibody combining site of the receptor molecule; and (c) maintaining the contact for a predetermined time period (typically about 10 minutes to about 12 hours, preferably, between 30 minutes and 4 hours) sufficient (i) for the second antibody combining site of the composition to bind to the tumor cell-associated antigen, and (ii) for the first antibody combining site to activate cytotoxic effector T lymphocytes that cytotoxically react with the antigen-bearing tumor cells.

The contacting in the above method can occur by admixture of the composition in vitro with a tumor cell culture where the source of cytotoxic effector T lymphocytes is supplied exogenously to the cell culture. Alternatively, the composition can be admixed in vivo, as by injection, with the blood stream of a host animal having a tumor bearing the tumor cell-associated antigen and whose immune system supplies an endogenous source of cytotoxic effector T lymphocytes. The method can further include the steps of periodically repeating steps (b) and (c) above until substantially all of the tumor cells have been killed.

The results of such a method for killing tumor cells are shown in Table III discussed hereinafter and in FIGS. 8–10.

The results discussed hereinafter illustrate that ligand molecules of this invention and a composition of the present invention that contains the ligand molecules in an effective amount focuses a strong T cell response to a particular pre-selected target antigen. Those results also show that the T cell response effected lysis and killing of the target-bearing cells.

The studies described hereinafter are intended as illustrations of the invention and are not to be taken as limiting. These studies utilized ligand molecules one of whose antibody combining sites immunoreacts with (binds to) the precursor T cell receptor that binds to the H-2$^d$ antigen, but not with the H-2$^b$ or H-2$^k$ antigens, and thereby not with the induces or activates the resting, precursor T cell into a cytolytic state. The second, exemplary, antibody binding site immunoreacts with (binds to) the Thy-1.1 antigen, but not the Thy-1.2 antigen. The Thy-1.1 antigen is an antigen expressed by almost all murine T cells.

The two ligand molecules described hereinafter were admixed with one of two resting, precursor, cytolytic T cell clones denominated G4 and OE4. Clone G4 cells are bound by Mab F9A7.3, are not bound by Mabs F23.1 or F23.2 and do not contain the Thy-1.1 antigen. The reactivity of the G4 cells may thus be described F9A7.3$^+$, F23.1$^-$, and F23.2$^-$, and Thy-1.1. Reactivity for the OE4 cells may be expressed as F9A.73$^-$, F23.1+, F23.2+, and Thy-1.1−, using similar nomenclature.

C. Discussion of Results

Specific results obtained using the ligand molecules of this invention and compositions containing those ligand molecules are described hereinafter in Section II. The discussion below summarizes those results and their implications.

Haskins et al., *J. Exp. Med.*, 160, 452 (1984) reported preparation of a rat monoclonal antibody that immunoreacted with the antigen receptor on about 20 percent of BALB peripheral T cells by immunizing a rat with antigen receptor material isolated by affinity adsorption from a BALB/c derived T helper hybridoma. Interestingly, the determinant recognized by that rat monoclonal antibody, denominated KJ16-133, was not expressed on the T cells of a few strains of mice; i.e., C57L/J, C57BR and SJL/J. These allelic differences in expression were utilized to make a number of allogeneic immunizations, the results of which are discussed in detail hereinafter. KJ16-133 negative (KJ16-133−) strains were immunized with the peripheral T cells from KJ16-133 positive (KJ16-133+) strains. It was anticipated that antiserum and monoclonal antibodies with similar specificity to KJ16-133 would be generated and also, on the assumption that other allotypic differences would be expressed on more than 20 percent of T cells, that other antibodies from these immunizations would be generated that would react with different subsets of T cells and possibly all T cell antigen receptors.

The results discussed hereinafter illustrate that immunization of C57L/J mice with BALB.B peripheral T cells results in the production of alloantisera that immunoprecipitate the T cell antigen receptor from heterogeneous BALB T cells. Two monoclonal antibodies, Mab F23.1 and Mab F23.2, were isolated that also immunoprecipitated the T cell receptor. Both monoclonal antibodies reacted with only a fraction of peripheral T lymphocytes; Mab F23.1 reacted with about 25 percent of lymph node T cells in BALB.B mice, while Mab F23.2 reacted with about 15 percent.

It was also shown in fluorescent staining experiments that the T cells recognized by the monoclonal antibodies F23.1 and F23.2, and those recognized by KJ16-133, were most likely the same T cell subpopulation, as Mab F23.1 stained about 25 percent of the cells, Mab F23.2 stained about 15 percent and Mab KJ16-133 stained about 20 percent. Mixing the antibodies in any combination did not result in additive staining. Thus, the three monoclonal antibodies, although obviously different in the number of cells with which they reacted, all recognized a population of T cells contained within the population recognized by Mab F23.1.

Figure 7:
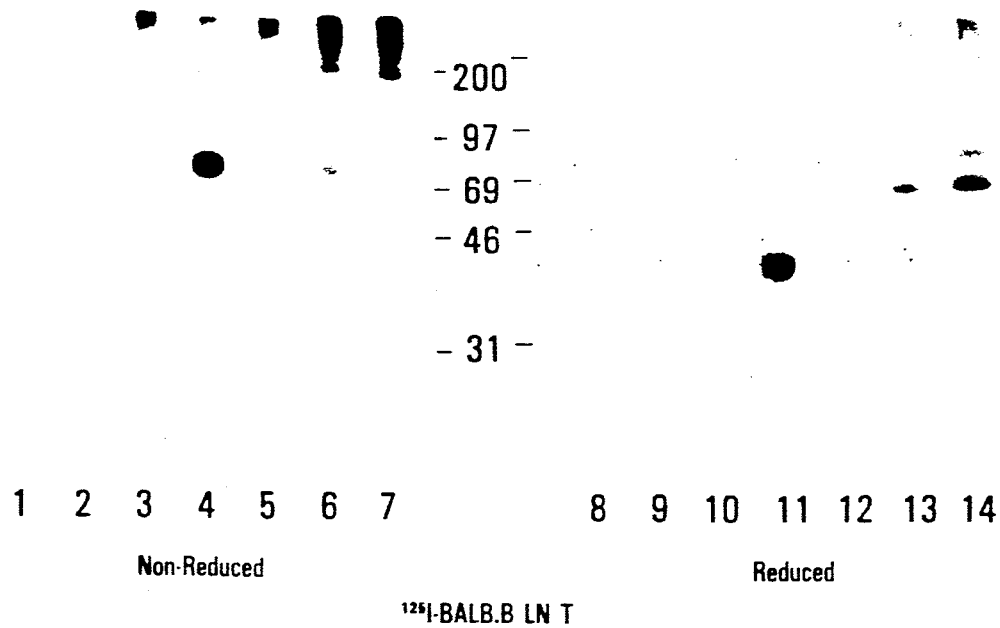
FIG. 7 is a photograph of an autoradiograph illustrating that the antiserum from mouse C3 and the monoclonal antibody F23.1 recognized the same subset of T cell receptors. Nylon wool-purified T cells from BALB.B mice were surface radioiodinated and lysed. Lysates shown in lanes 1, 2, 4, 8, 9 and 11 were precleared with medium; lysates in lanes 3, 5, 10 and 12 were precleared with Mab F23.1; lysates in lanes 6, 7, 13 and 14 were precleared with Mab F23.2. Material analyzed on 7.5-15 percent SDS-PAGE as shown in FIG. 7 was precipitated with medium, lanes 1 and 8; antiserum C3, lanes 2, 3, 9 and 10; Mab F23.1, lanes 4, 5, 6, 11, 12 and 13; and, Mab F23.2, lanes 7 and 14. Precipitates were run under non-reducing (lanes 1-7) or reducing (lanes 8-14) conditions.

Screenings were also undertaken to determine whether the whole antiserum, C57L/J anti-BALB.B, contained extra reactivity for T cell receptors. Such screenings could not be accomplished by fluorescent staining because of the unknown complexity of the whole serum, but it was accomplished by immunoprecipitation preclearing as is shown in FIG. 7.

The results of the screenings, discussed in detail hereinafter, showed that the monoclonal antibody F23.1 could completely preclear the surface-labelled receptor material that was immuno-precipitated by the whole antisera. In other screenings, Mab F23.1 also completely precleared for Mab KJ16-133 or Mab F23.2. Thus, it was concluded that the serum did not contain any additional reactivity with BALB.B antigen receptors, and this may have implied that the two strains, C57L/J and BALB.B, did not show T cell antigen receptor allotypic differences other than the one identified by Mab KJ16-133. It should be noted that peripheral T cells from BALB.K or B10.BR mice were also injected into C57BR recipients (these pairs also differed in the expression of Mab KJ16-133) and, although the sera were complex in their immunoprecipitation profiles, there was no evidence for any reactivity with the T cell receptor. Thus, the failure to make antibodies could not be taken as strong evidence that no further allotypic differences existed between these strains.

It is not known with what region of the T cell antigen receptor molecule the three monoclonal antibodies reacted. There is some preliminary evidence that the serological allotypic difference co-mapped with the beta chain locus of the T cell receptor on chromosome 6. The beta chain locus was shown to include two constant region genes that differed in four amino acid substitutions, up to ten functional J regions, a number of D segment genes, as well as an unknown number of V genes, Malissen et al , *Cell*, 37, 1101 (1984); Gascoigne et al., *Nature*, 310, 387 (1984); and Kavaler et al., *Nature*, 310, 421 (1984).

The three monoclonal antibodies that identified an allotypic difference on the T cell receptor all showed a temperature dependence in their binding to the surface of viable cells, as was reported by Haskins et al., *J. Exp. Med.*, 160, 452 (1984), for Mab KJ16-133, but they stained reproducibly different fractions of T cells. In fluorescent staining screenings, Mab F23.1 consistently reacted with a larger fraction of T cells than the monoclonal antibodies KJ16-133 and F23.2. These differences suggest that the determinant recognized is present on the part of the molecule that is at least affected by receptor sequence variability; i.e., a J region segment or possibly a V region family. On the other hand, it also suggests that the determinant is on a constant region of the molecule (one of the two C constant regions, for example), and that the differences in binding are explained simply on the basis of affinity of the antibodies. The latter does not seem likely since the antibody, Mab F23.2, that stained the smallest fraction of T cells, stained this fraction as brightly as did Mab F23.1. The results indicate that the most likely site for the localization of the determinant is a J region that is not expressed or is different in C57L/J mice.

Although a number of CTL clones utilized in screenings were all negative for reactivity with Mab F23.1, cell sorting screenings were performed that suggested that this determinant was present on CTL precursors. The frequency of responding CTL measured in limiting dilution was the same in Mab F23.1 positive and Mab F23.1 negative populations. It was known that this determinant was also present on Class II restricted helper T cells, Haskins et al., *J. Exp. Med.*, 160, 452 (1984). Thus, the determinant did not seem to discriminate between the two major populations of T cells, killers and helpers.

Furthermore, the monoclonal antibody F23.1 was capable of blocking specific lysis mediated by a F23.1 positive line but had no effect on F23.1 negative CTL lines. Fractionating peripheral T cells with antibodies specific for Lyt-2 or L3T4, also showed that this allotypic determinant was present on both populations, Roehm et al., *Cell*, 38, 577 (1984).

Additionally, it was found that, while most strains were positive for reactivity with Mab F23.1, there were strain differences in the fraction of peripheral T cells that reacted. C3H.OH mice, for example, contained a large number of peripheral T cells that react with the monoclonal antibody. Such results are described hereinafter in Section II.

As it would be desirable, in some disease situations, to be able to focus a strong T cell response at a chosen target, further screenings were performed that demonstrated that the specificity of T lymphocytes to eliminate unwanted cells and the availability of monoclonal antibodies to cause beneficial inflammatory reactions could be combined. The results described in detail hereinafter demonstrate that ligand molecules of the present invention, that may also be referred to as hetero-conjugates of monoclonal antibodies or hybrid antibodies, in which a first antibody combining site binds to a T cell receptor complex structure and is linked to a second antibody combining site that binds to any chosen target cell-associated antigen, are able to focus T cells to act at the targeted site. Monoclonal antibodies directed against a T cell receptor, such as the anti-allotype utilized in the screenrngs, were mitogenic for resting T cells and could be used to induce cytotoxic effector T cells that bore the T cell receptor determinant and that could then be directed to the target to lyse it by the hybrid antibody.

Monoclonal antibodies directed against determinants of the T cell receptor complex of cytotoxic T lymphocytes or helper T cells are known to be able to mimic the effect of antigen in many ways. For example, anti-idiotypes in an appropriate form were reported to activate idiotype-positive T cell clones to release soluble factors such as interleukin-2 (Il-2), Kappler et al., *Cell*, 34, 727 (1983) and Meuer et al., *J. Exp. Med.*, 158, 988 (1983), or gamma-interferon (gamma-IFN), Staerz et al., *Proc. Natl. Acad. Sci. (USA)*, 81, 1799 (1984), and to proliferate, Kaye et al., *J. Exp. Med.*, 158, 836 (1983). In addition, recent reports have suggested that anti-idiotype on the surface of a cell rendered the cell sensitive to recognition and lysis by an idiotype-positive CTL clone, that B cell hybridomas producing anti-idiotype could serve as targets for idiotype positive CTL, Ertl et al., *Proc. Natl. Acad. Sci. (USA)*, 79, 7479 (1982) and Lancki et al., *Fed. Proc.*, 43, 1659 (1984), and that anti-T3 antibodies fixed covalently to cells converted them to sensitive CTL targets, Martz, *Immunol. Today*, 5, 254 (1984). However, the ligand molecules of the present invention were not suggested by the above or other reports known to the present inventors, nor are the effects obtained using the instant ligand molecules suggested by those reports.

The results are described first as to the preparation and characterization of Mabs F23.1 and F23.2, followed by a description of results from studies using ligand molecules of this invention.

II. RESULTS

A. Alloantibodies to the Murine T Cell Antigen Receptor

1. Immunization of C57L/J Mice With BALB.B T Lymphocytes

Recently, a rat-rat monoclonal antibody, KJ16-133, described in Haskins et al., *J. Exp. Med.*, 160, 452 (1984), was derived from rats injected with partially purified T cell antigen receptor material. This antibody reacted with the heterodimer receptor of about 20 percent of peripheral lymphocytes in most common laboratory mice, including BALB.B, but was absent in a few strains including C57L/J. This differential expression was used in screenings to produce murine monoclonal antibodies against the T lymphocyte subpopulation in BALB.B mice.

Nylon wool-purified T lymphocytes from normal BALB.B mice suspended in balanced salt solution were injected intra-peritoneally into C57L/J mice. After three injections at 10-day intervals, the mice were bled and the sera were tested for their activity against the T lymphocyte antigen receptor.

Due to the uncertainty as to whether the antisera interfered with any T cell function, the sera were screened by immunoprecipitation. Lymph node cells from normal BALB.B mice were surface-labelled and lysates were prepared, and were then tested for immunoprecipitation using these sera. As shown in FIG. 1, four out of five immunized C57L/J mice produced antibodies that reacted with the heterodimeric structure characteristic of the T cell antigen receptor precipitating a band of a molecular weight of approximately 82,000 daltons under non-reducing conditions, and a broad band of approximately 42,000 daltons under reducing conditions.

However, in this series of immunizations, one mouse showed no detectable antibodies against the T cell antigen receptor as tested by immunoprecipitation but showed several bands of different molecular weight in no way resembling the T cell antigen receptor (FIG. 1, lanes 4 and 9). In the non-reducing situation, a major band with a molecular weight of about 128,000 daltons and a minor duplet at 100,000 and 92,000 daltons could be identified. Upon reduction, the major band was unchanged, whereas the duplet could only be recognized as a single band at 92,000 daltons.

In the next screening, it was determined whether the sera reacted with the T cell antigen receptors of all T lymphocytes in BALB.B mice. A set of monoclonal antibodies against the clonotypic structure of G4, a cloned BALB.B CTL line that is specific for murine major histocompatibility complex $H-2^d$, were produced. FIG. 2 shows that neither of two tested sera reacted with the surface structure on G4. As a control, a precipitate of the T cell antigen receptor of this CTL clone was produced using the clonotypic murine monoclonal antibody, F9A7.3 that immunoreacts with (binds to) a receptor structure of resting T cells. These same sera also failed to precipitate the receptor from another functional BALB.B. CTL clone, B10. These results indicated that the antisera reacted with only a subpopulation of BALB.B T lymphocyte antigen receptors.

2. Production of Monoclonal Antibodies

After it had been allowed to rest for 4 weeks (maintained for a time period sufficient to induce production of antibodies), C3, a hyperimmunized C57L/J mouse with a high titer of immunoprecipitating antibodies in the serum, was given a final intravenous immunization with viable BALB.B T lymphocytes. Spleen cells from this animal were used for fusion three days later as described in detail in Section III hereinafter.

About 700 wells positive for growth were screened. In this fusion, two different hybridoma clones were obtained that secreted antibodies reacting wtih BALB.B T lymphocytes as analyzed by indirect immunofluorescence. Both hybridomas, denominated F23.1 and F23.2 as are their secreted monoclonal antibodies, denominated Mab F23.1 and Mab F23.2, respectively, proved to be relatively unstable and required several cloning procedures until a continuously secreting subclone was established.

Figure 3:
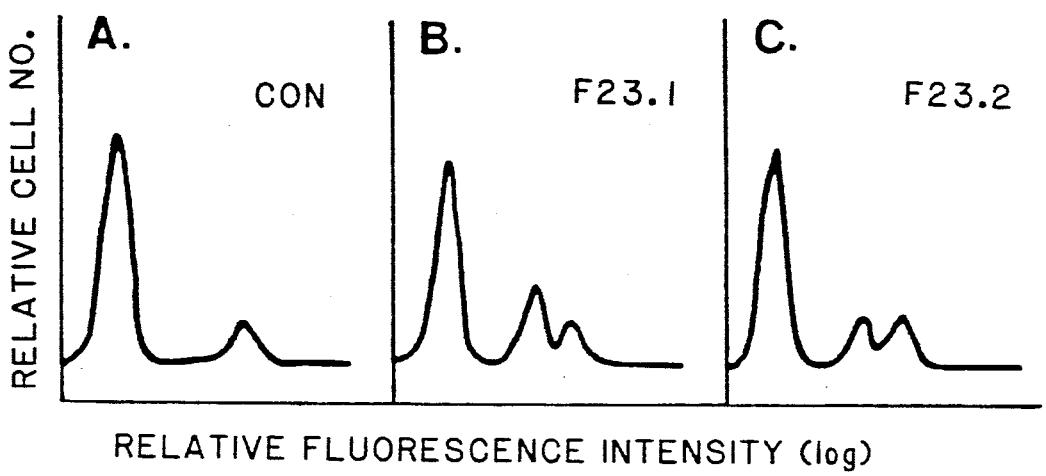
FIG. 3 is a series of graphs illustrating the fluorescence profiles of BALB.B lymph node cells stained with Mab F23.1 (B), Mab F23.2 (C) followed by fluorescein-coupled 9oat anti-mouse immunoglobulin (FITC-GAMIG) compared with the same cells stained with FITC-GAMIG alone (A).

All supernatants were screened by assaying their contents for antibodies that bind to viable lymph node cells or nylon wool column-enriched T lymphocytes using an indirect immunofluorescence assay. FIG. 3 shows the fluorescence profile of unseparated lymph node cells of a BALB.B mouse using the two monoclonal antibodies, F23.1 and F23.2.

Approximately 23 percent of the fluorescing cells were B cells as judged by staining with fluorescein-coupled goat anti-mouse immunoglobulin (FITC-GAMIG) alone (FIG. 3, panel A). Using supernatants containing the monoclonal antibodies F23.1 or F23.2, a second fluorescent peak appeared that was less bright than the B cell population but was clearly distinct from the non-stained cells. About 25 percent and 15 percent of surface Ig-negative cells; i.e., T lymphocytes, bound monoclonal antibodies F23.1 or F23.2, respectively. Since the bright B cell population did not change fluorescence intensity during these screenings, neither Mab F23.1 nor Mab F23.2 appeared to react with specific surface antigens of the B cells.

Figure 4:
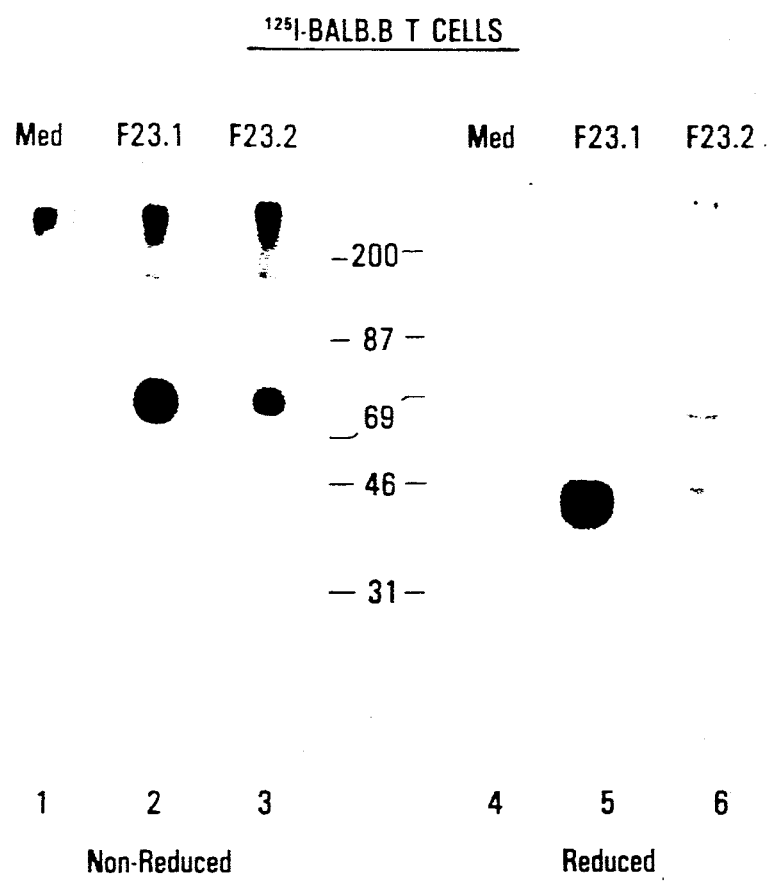
FIG. 4 is a photograph of an autoradiograph illustrating the precipitation by moloclonal antibodies of the heterodimeric structure of the T lymphocyte antigen receptor of surface radioiodinated lymph node T cells. The monoclonal antibodies F23.1 and F23.2 precipitated the T cell antigen receptor from peripheral T cells. Nylon wool purified T cells from BALB.B mice were surface radioiodinated and lysed. The precleared lysates were immunoprecipitated with growth medium (lanes 1 and 4), with the Mab F23.1 (lanes 2 and 5) and with the Mab F23.2 (lanes 3 and 6). The precipitates were analyzed on SDS-PAGE both under non-reducing (lanes 1 through 3) and reducing (lanes 4 through 6) conditions.

Both monoclonal antibodies precipitated the heterodimeric structure of the T lymphocyte antigen receptor of surface radioiodinated lymph node T cells as shown in the electrophoresis screenings on polyacrylamide gels of FIG. 4, lanes 2, 3, 5 and 6, in contrast to a control precipitated with growth medium alone (lanes 1 and 4). Nylon wool-purified T lymphocytes from BALB.B lymph nodes and spleens were used for these screenings as representative of a heterogeneous population of peripheral T lymphocytes.

When the intensity of precipitates with Mab F23.1 (lanes 2 and 5) were compared to those achieved with Mab F23.2 (lanes 3 and 6), darker bands were clearly shown for precipitates of Mab F23.1, both in the non-reducing and reducing cases. These results supported the evidence from the indirect immunofluorescence screenings (FIG. 3) that Mab F23.1 reacted with a larger subpopulation of peripheral T lymphocytes than did Mab F23.2.

3. Temperature Dependence of Mab F23.1 and Mab F23.2 Binding

Figure 5:
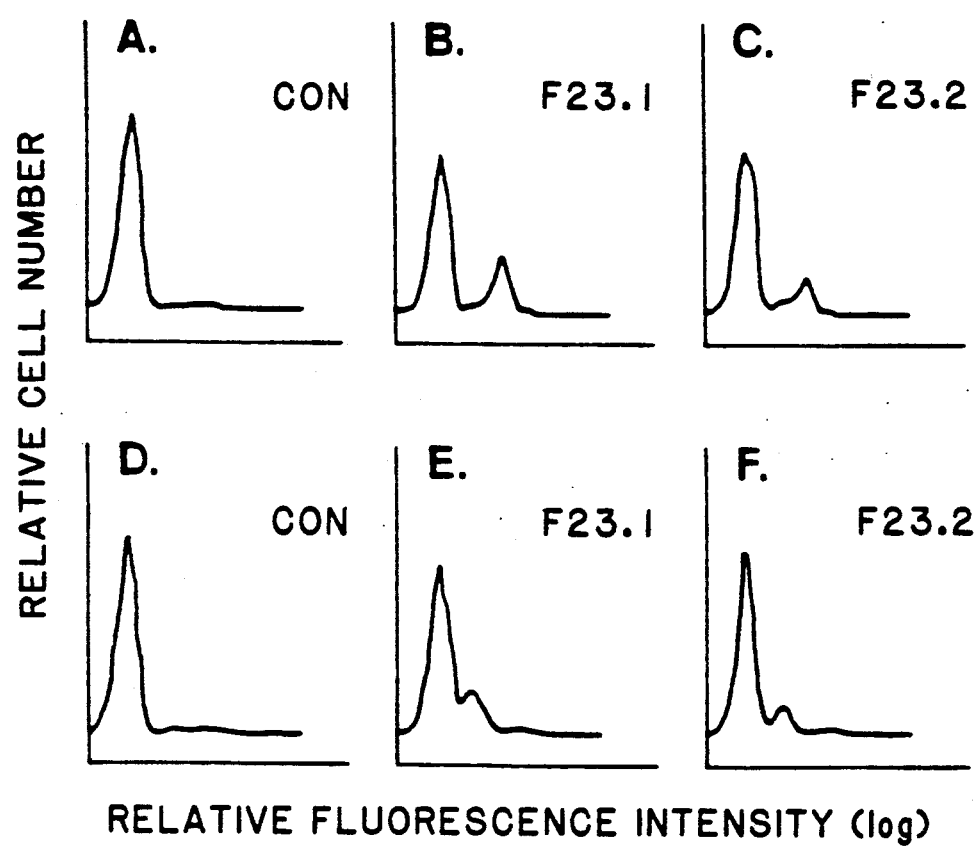
FIG. 5 is a series of graphs illustrating that the staining of peripheral T cells by monoclonal antibodies F23.1 and F23.2 is temperature dependent. BALB.B T lymphocytes purified on a nylon wool column were admixed and maintained (incubated) with growth medium alone (panels A and D), with Mab F23.1 (panels B and E) and with Mab F23.2 (panels C and F) at 37° C (panels A, B and C) or on ice (panels D, E and F) for 30 minutes followed by staining with FITC-GAMIG at room temperature. Washed cells were analyzed on a fluorescence-activated cell sorter.

It was reported in Haskins, et al., J. Exp. Med., 160. 452 (1984), that the rat monoclonal antibody KJ16-133 was temperature-sensitive in its binding properties, exhibiting markedly reduced binding to viable T cells at low temperatures. FIG. 5 illustrates the same property for both monoclonal antibodies F23.1 and F23.2.. Whereas incubation at 37° C. during the whole period of exposure of nylon wool purified BALB.B T lymphocytes to Mab F23.1 and Mab F23.2 resulted in the usual number of bright T lymphocytes, 25 percent and 15 percent (FIG. 5, panels B and C), respectively, incubating the cells on ice with Mab F23.1 and with Mab F23.2 shifted the peak of stained cells to lower intensity in both cases (panels E and F). Only a small number, 5 percent, of residual B lymphocytes could be detected when the first antibody was omitted (panels A and D). This result illustrates that the antigenic sites for Mab F23.1 and Mab F23.2 exposed at the cell surface were less accessible to the antibodies at low temperatures and/or that their configuration showed temperature dependent changes interfering with antibody binding.

4. Overlapping Populations Detected by Monoclonal Antibodies F23.1, F23.2 and KJ16-133

Figure 6:
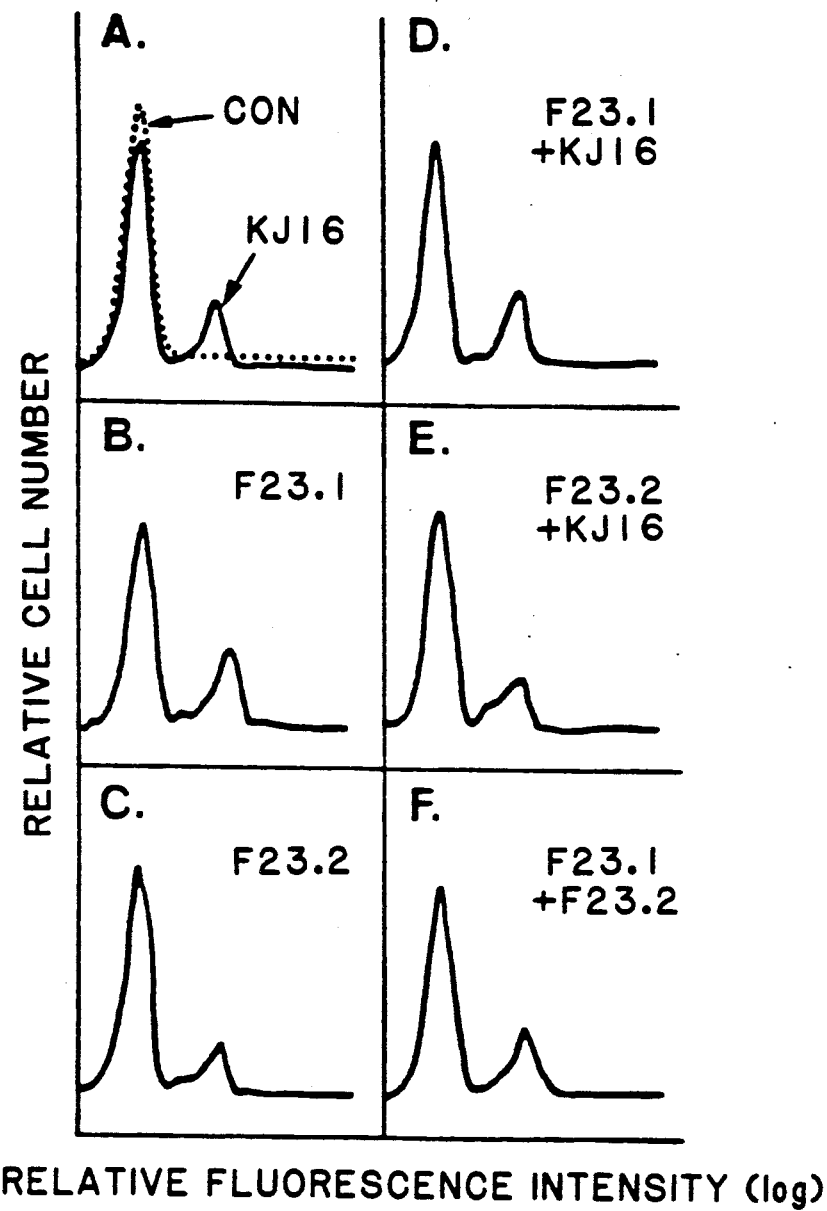
FIG. 6 is a series of graphs illustrating that the T cell populations stained by Mab F23.2 and rat antibody KJ16-133 were part of the Mab F23.1-positive population. BALB.B peripheral T cells were stained with KJ16-133 (panel A), Mab F23.1 (panel B), Mab F23.2 (panel C) alone or with Mab F23.1 together with KJ16-133 (panel D), Mab F23.2 together with KJ16-133 (panel E), or Mab F23.1 together with Mab F23.2 (panel F), at 37° C. followed by FITC-GAMIG. As a control, a first antibody was omitted (panel A, dotted line). FITC-GAMIG alone recognized 5 percent of the cells, Mab F23.1 as first antibody 25 percent, Mab F23.2 15 percent and KJ16-133 20 percent, Mab F23.1 together with KJ16-133 15 percent, Mab F23.2 together with KJ16-133 20 percent and Mab F23.1 together with Mab F23.2 25 percent.

The assumption that murine monoclonal antibodies could be raised against the T cell antigen receptor of BALB.B mice based on data about strain differences in expression of the Mab KJ16-133 antigen in C57L mice, seemed to be negative. Indirect immunofluorescence screenings showed that the sizes of the different subpopulations recognized by the respective antibodies varied; the monoclonal antibody F23.1 stained about 25 percent, KJ16-133 about 20 percent and F23.2 about 15 percent of BALB.B peripheral T lymphocytes. FIG. 6 shows the results of a screening of the extent of overlap of these different cell populations.

In this indirect immunofluorescence assay, the second antibody (FITC-GAMIG) alone labelled about 5 percent of all cells, identifying them as remaining B cells (FIG. 6, panel A, dotted line). Using Mabs F23.1, KJ16-133, and F23.2 as first antibody produced the same results as stated above.

When the primary admixture and its maintenance to provide for immunoreaction (incubation) was done with two different antibodies at the same time, no additive staining was achieved as both combinations, Mab F23.1 together with Mab KJ16-133 and Mab F23.1 together with Mab F23.2, recognized about 25 percent of all peripheral T lymphocytes, while Mab F23.2 and Mab KJ16-133 together stained about 20 percent. These results demonstrate that the three populations not only overlapped, but that the smaller populations, Mab KJ16-133 positive cells and Mab F23.2 positive cells, were part of the larger Mab F23.1 positive population. The brightness of the T cell peak did not change but was equal in all panels, indicating that the total number of bound antibodies did not increase with the combination of antibodies, suggesting that all three monoclonal antibodies competed for binding.

5. Strain Distribution of Mab F23.1

Not all inbred mouse strains expressed the antigenic determinant recognized by Mab F23.1, as can be clearly seen in Table I below:

TABLE I

Expression of the Antigen Detected by Mab F23.1 on Lymph Node Cells of Different Strains*

| Mouse Strain | Percent cells positive for | | Percent Ig-negative cells positive for |
|---|---|---|---|
| | FITC-GAMIG alone | F23.1 | F23.1 |
| BALB/c | 16.3 | 40.1 | 28 |
| C57BL/10 | 26.3 | 40.3 | 19 |
| CBA/J | 15.9 | 35.9 | 24 |
| C57BR/cdJ | 15.8 | 16.3 | 1 |
| C57L/J | 18.3 | 18.8 | 1 |
| SJL/J | 13.5 | 12.9 | 0 |
| A.TL | 31.3 | 47.2 | 23 |
| DBA/2 | 16.2 | 39.1 | 27 |
| C3H.OH | 17.4 | 47.3 | 36 |

*Unseparated lymph node cells from different mouse strains were prepared by standard techniques [Julius et al., Eur. J. Immunol., 3, 645 (1973)] and stained with the monoclonal antibody F23.1 (final dilution of the culture supernatant was ½) for 30 minutes at 37° C., followed by FITC-GAMIG (final dilution of 1/50) for 30 minutes at room temperature. After thorough washing, cells were fixed and analyzed on a fluorescence activated cell sorter.

As shown in Table I, in indirect immunofluorescence, lymph node cells from C57Br/cdJ, C57L/J and SJL mice did not show detectable levels of Mab F23.1 staining when compared with FITC-GAMIG alone. All other tested strains, BALB/c, C57BL/10, CBA/J, A.TL, DBA/2 and C3H.OH, showed a population positive for reaction with Mab F23.1, although the fraction of Ig-negative cells stained differed between the different strains, varying from a low of 19-23 percent in C57BL/10 and A.TL mice to a high of 36 percent in C3H.OH mice.

6. Comparison of the Reactivity of the Whole Antiserum C3 and the Monoclonal Antibody The antiserum C3 from a C57L/J mouse immunized with BALB.B T lymphocytes stained 60 percent of all BALB.B T lymphocytes in indirect immunofluorescence. Since this could have been due to reactivities to other surface antigens, immuno precipitation was utilized to screen the relationship between the T cell antigen receptors bound by the antiserum, C3, and by the monoclonal antibody, F23.1. FIG. 7 shows that lysates thoroughly pre-precipitated with F23.1 antibody were free of an T cell antigen receptor recognized by the C3 serum.

BALB.B T lymphocytes were surface radioiodinated, lysed and pre-precipitated twice with supernatants containing F23.1 monoclonal antibodies as described in detail in Section III hereinafter. The precleared lysate was re-precipitated either with the antiserum C3 or again with F23.1. The washed precipitates were analyzed on a SDS-PAGE both under reducing and non-reducing conditions.

Lanes 3 and 10 of FIG. 7 illustrate that the antiserum C3 did not detect any remaining T cell antigen receptor. Lanes 5 and 12 show that the precipitation with Mab F23.1 was complete, as the characteristic heterodimer could not be bound anymore by Mab F23.1 after pre-precipitation with the same antibody. Lanes 4 and 11 were obtained from lysates precleared with rabbit antiserum against murine IgG (RAMIG) beads alone and then precipitated with Mab F23.1, and dark bands were evident at 82,000 and 42,000 daltons, respectively, under non-reducing or reducing conditions. Precipitates using C3 as a source of first antibody gave the same results after nonspecific preclearing (lanes 2 and 9).

These results illustrate that the antiserum C3 did not recognize T cell antigen receptors on a T cell population much larger than the one identified by Mab F23.1. As a control study, Mab F23.2 precleared lysates, free of any remaining activity for this antibody, still contained material precipitated by Mab F23.1 (FIG. 7, lanes 7 and 14, 6 and 13, respectively). Additionally, other preclearing experiments have shown that monoclonal antibody F23.1 completely removed the T cell receptor material reactive with the KJ16-133 antibody described in Haskins et al., *J. Exp. Med.*, 160, 452 (1984).

7. Both Mab F23.1 Positive and Mab F23.1 NegativeT Cells Contain CTL Precursors Six out of six CTL clones that were screened for reactivity with the F23.1 monoclonal antibody did not express the determinant. Two clones were from BALB.B mice, specific for MHC H-1$^d$; one was from (B10.D2×B10.BR)F$_1$, specific for BALB/c; and three were from C57BL/6, specific for BALB.B.

In order to screen whether Mab F23.1 positive T cells contained CTL, Jlld-plus-complement treated lymph node cells of BALB.B mice were sorted into Mab F23.1 positive and negative fractions. Twenty-four percent of the T cells were positively stained and were sorted for the brightest 19 percent and the dullest 69 percent. Reanalysis immediately after the sorting showed less than 5 percent contamination between the fractions. Both populations were activated in limiting dilution conditions with irradiated BALB/c spleen cells.

As shown in Table II below, the frequency of responding CTL was the same in both populations. Bulk populations of Mab F23.1 positive and Mab F23.2 negative CTL lines were established by weekly reactivation in MLC that did not change phenotype as assayed by indirect immunofluorescence with Mab F23.1. After three reactivations, the specific cytolysis mediated by the Mab F23.1 positive CTL line was inhibited three-fold by admixture with the monoclonal antibody F23.1. The specific lysi mediated by the Mab F23.1 negative line was not inhibited by F23.1 antibody.

TABLE II

| Limiting Dilution Analysis of CTL Precursor Frequency of Mab F23.1 Positive and Negative T Cells | | | |
|---|---|---|---|
| Cell Population$^a$ | Anti-H-2$^d$ CTL precursor frequency | r$^{2b}$ | a$^c$ |
| F23.1 positive | 1/1770 | 0.99 | 1.05 |
| F23.1 negative | 1/1717 | 0.97 | 1.01 |

$^a$BALB B lymph node cells were enriched for T cells by treatment with the monoclonal antibody Jlld and complement. The cells were stained for Mab F23.1 by indirect immunofluorescence and sorted into Mab F23.1 positive and Mab F23.1 negative populations. Sorted populations were activated under limiting dilution conditions with irradiated BALB/c (H-2$^d$) spleen cells for 7 days. Cells were assayed in $^{51}$Cr-labelled P815 and EL4 targets.
$^b$"r$^2$" is the correlation coefficient.
$^c$"a" is the y-axis intercept calculated by linear regression as described in Section III.A.9, hereinafter.

Similar results were obtained by sorting (SJL×BALB/c)F$_1$ peripheral T cells into Mab F23.1 positive and negative fractions. Both populations gave good CTL responses to H-2$^b$ activators in bulk cultures. Again, the frequency of CTL precursors measured in limiting dilution differed less than by a factor of two.

B. Targeting Sites for Lysis By Ligand Molecules That Induce Cytotoxic Effector T Lymphocytes Further screenings were undertaken to determine whether Mab F23.1, the anti-allotypic Mab, could focus CTL onto a target cell. The surfaces of various cell types were directly coupled with the isolated Mab using a heterobifunctional cross linker.

The cell line denominated OE4 is a CTL clone of C57BL/6 (H-2$^b$) origin with lytic specificity for H-2$^d$-bearing cells. The antigen receptor of clone OE4 bears the allotypic determinant recognized by Mab F23.1.

Figure 8:
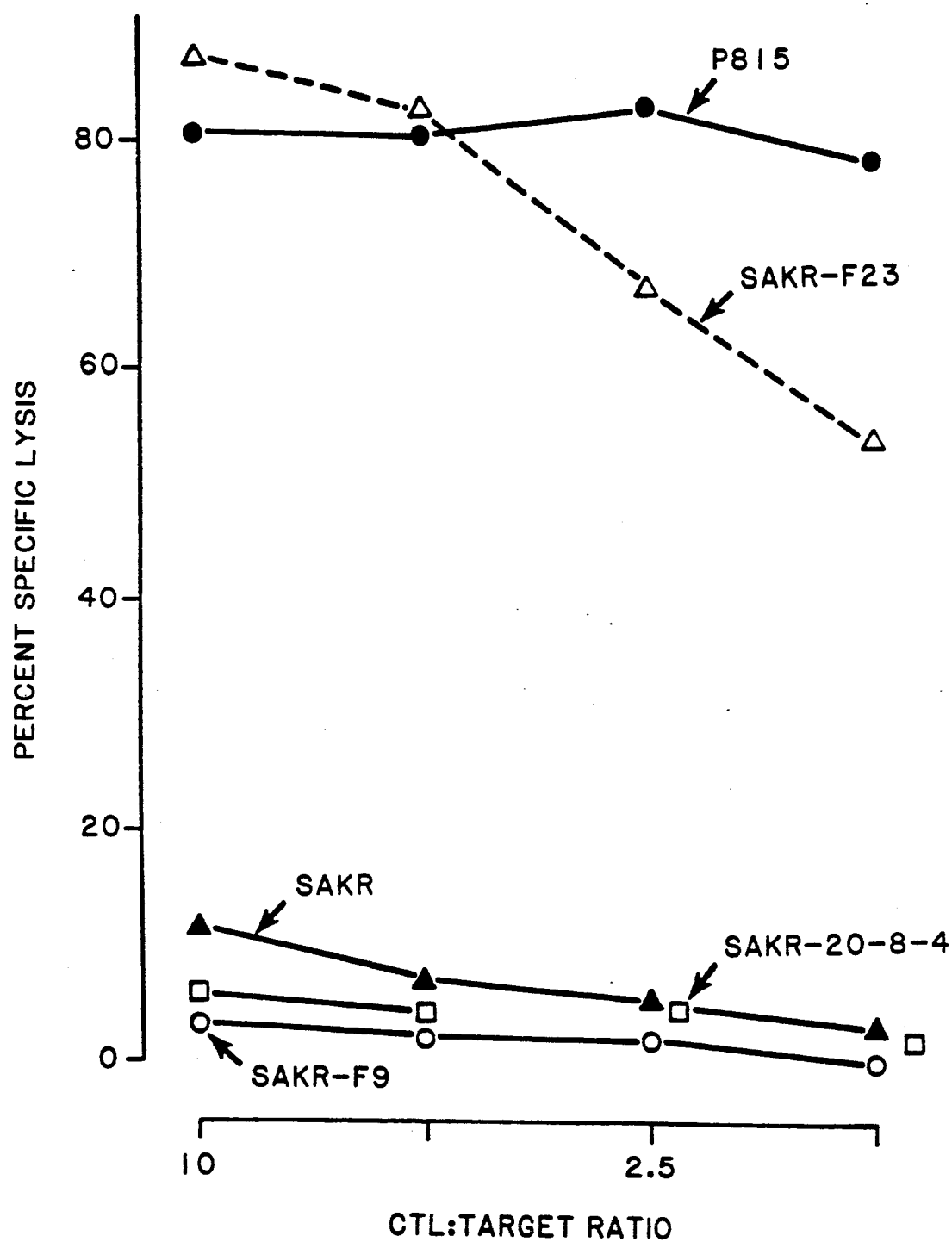
FIG. 8 is a graph illustrating that the anti-receptor allotype monoclonal antibody F23.1 coupled to a cell surface rendered the cell susceptible to lysis by an allotype positive cytotoxic effector T lymphocyte (CTL) clone, OE4. Mab F23.1 (IgG2a) and Mab F9A7.3 (IgG1), monoclonal antibodies specific for an idiotypic determinant on CTL clone G4 [Staerz et al., *Proc. Natl. Acad. Sci. (USA)*, 81, 1799 (1984)], and the anti-H-2$^b$ Mab, 20-8-4 (IgG2a) [Ozato et al., *J. Immunol.*, 126, 317 (1981)] produced in C3H mice were purified from ascites fluids on *Staphylococcus aureus* Protein A-Sepharose (Protein A-Sepharose). Antibodies were reacted with the heterobifunctional cross-linker N-succinimydyl-3-(1-pyridyldithio)-proprionate (SPDP Sigma, St. Louis, MO) according to Carlsson et al., *Biochem J.*, 173, 723 (1978). A three-fold molar excess of SPDP was used to introduce 2-3 groups per antibody. The modified, hybrid antibody was reacted with S.AKR lymphoma cells (H-2$^k$, Thy 1.1) that had been pretreated with 0.5 millimolar (mM) dithiothreitol to introduce free sulphydryl groups at the cell surface [Jou et al., *Proc. Natl. Acad. Sci. (USA)*, 78 2493 (1981); Chen et al., *J. Exp. Med.*, 157, 772 (1983)]. After washing, $1 \times 10^4$ pre-labelled ($^{51}$Cr-sodium chromate) target cells were incubated at 37° C. with two-fold serial dilutions of the cytotoxic T lymphocyte (CTL) clone OE4 for 4 hours at 37° C. according to Staerz et al., *Proc. Natl. Acad. Sci. (USA)*, 81, 1799 (1984). Percent specific lysis of these target cells and of P815 (DBA/2, H-2$^d$), cell targets was calculated as described in Staerz et al., *Proc. Natl. Acad. Sci. (USA)*, 81, 1799 (1984). The CTL clone OE4 was isolated by limiting dilution from a C57BL/6 (H-2$^b$) anti-DBA/2 (H-2$^d$) mixed lymphocyte culture and was maintained by weekly subculture with irradiated DBA/2 spleen cells plus interleukin-2 (IL-2). OE4 reacted with the anti-allotypic Mab F23.1 and with the anti-H-2$^b$ Mab 20-8-4 but not with the anti-idiotypic Mab F9A7.3. Target cells were: P815 ●, S.AKR ▲, S.AKR coupled with Mab F23.1 (△), S.AKR coupled with Mab F9A7.3 (○) and S.AKR coupled with Mab 20-8-4 (□).
Figure 9:
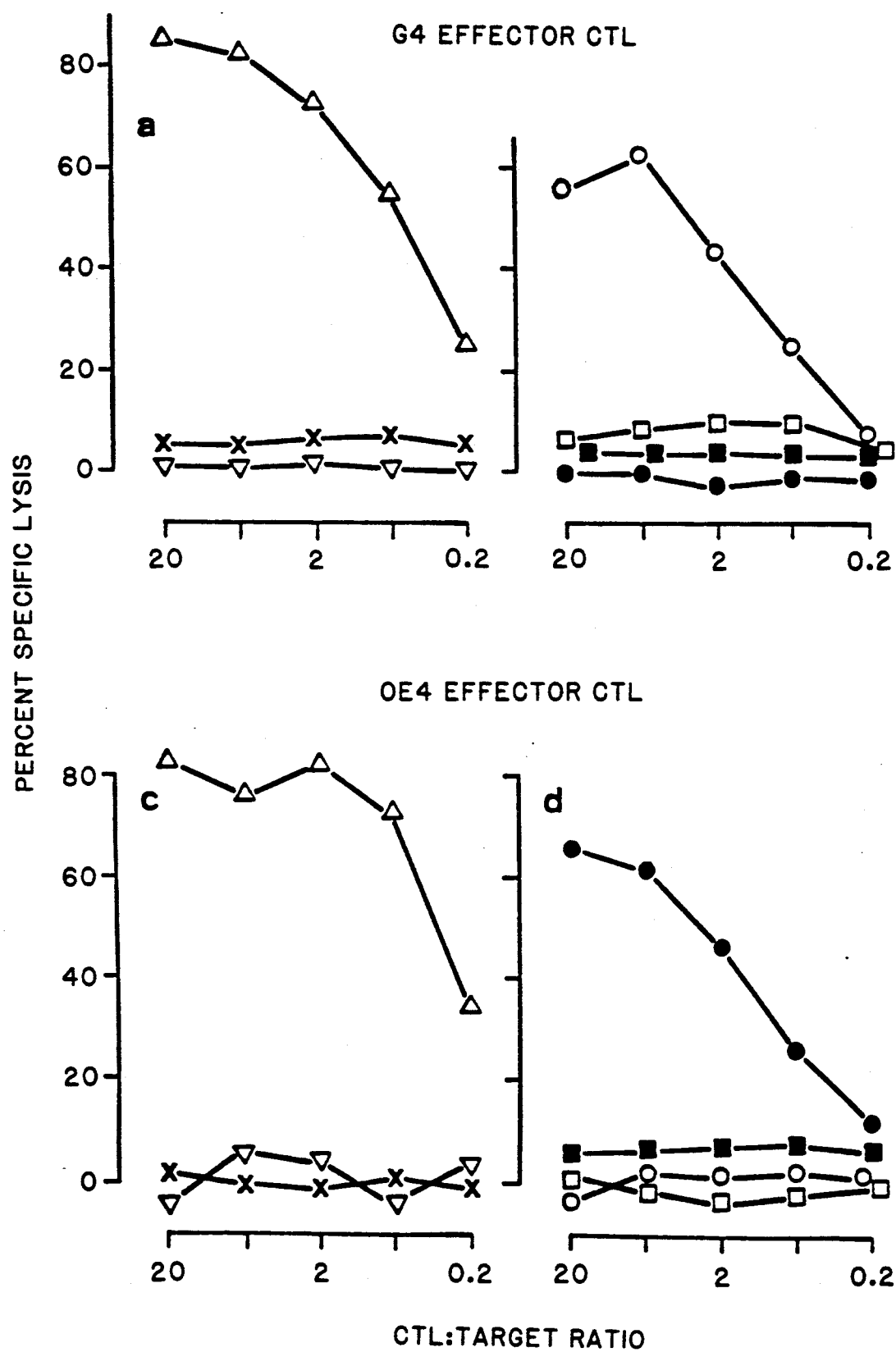
FIG. 9 is a series of graphs illustrating that heteroconjugates of Mabs (hybrid antibodies) could specifically target cells for CTL-mediated lysis. The monoclonal alloantibody 19E12 [Houston et al., *J. Immunol.*, 125, 837 (1980)] (IgG2a) specific for the Thy 1.1 alloantigen was purified from ascites fluid on Protein A-Sepharose, modifed with SPDP, according to Carlsson et al., *Biochem. J.*, 173, 723 (1978), and coupled to either Mab F23.1 or Mab F9A7.3 according to the Pharmacia Fine Chemicals (Piscataway, NJ) handbook on SPDP. The hybrid antibodies were used to coat $^{51}$Cr-labelled EL4 (H-2$^b$, Thy 1.2) and S.AKR (H-2$^k$, Thy 1.1) lymphoma cells by incubation at 37° C. for 20 minutes followed by washing. These target cells plus uncoated $^{51}$Cr-labelled S.AKR, EL4 and P815 (H-2$^d$) targets were assayed for lysis by serial three-fold dilutions of CTL for 4 hours at 37° C. Effector CTL clones were: a and b, G4 [BALB.B (H-2$^b$) anti-BALB/c (H-2$^d$)] that are positive for the idiotypic determinant recognized by Mab F9A7.3 [Staerz et al., *Proc. Natl. Acad. Sci. (USA)*, 81, 1799 (1984)], and unreactive with Mab F23; c and d, OE4 [C57BL/6 (H-2$^b$) anti-DBA/2 (H-2$^d$)] CTL clone are Mab F23+, F9A7.3. Target cells were P815 (H-2$^d$, △, S.AKR (H-2$^k$, △), EL4 (H, ▽), S.AKR incubated with 19E12-F23 ●, S.AKR incubated with 19E12-F9A7.3 (○), EL4 incubated with 19E12-F23 ■), and EL4 incubated with 19E12-F9A7.3 (□).

The data in FIG. 8 show that OE4 cells did not kill the lymphoma S.AKR [derived from AKR/J (H-2$^k$) mice] in a four hour cytotoxic assay, but did efficiently lyse P815 [DBA/Z, H-2$^d$] target cells from a mastocytoma. However, S.AKR cells that had been chemically coupled with Mab F23.1 were efficiently lysed by OE4. Target cells similarly coupled with the anti-idiotypic Mab F9A7.3 (that does not immunoreact with OE4 cells) were insensitive to OE4 effectors as were S.AKR cells coupled with an anti-H-2$^b$ Mab, 20-8-4, that did react with the H-2$^b$ molecules expressed by OE4.

Reciprocal results were obtained with the F9A7.3 idiotype positive, allotype negative CTL clone, G4 [BALB.B (H-2$^b$) anti-H-2$^d$]. F9A7.3-coupled cells were sensitive targets while Mab F23.1-and 20-8-4-coupled cells were not killed.

Thus, it was shown that Mabs directed against determinants on the T cell antigen receptor, when coupled to the surface of target cells, served to target cells for attack by CTL. Furthermore, an anti-H-2 Mab that reacted with the CTL did not serve to trigger lysis.

Screenings were then undertaken to determine whether ligand molecules of this invention (hybrid antibodies) would be able to specifically target cells for destruction by CTL. In the ligand molecules, formed as described in detail in Section III hereinafter, one of the monoclonal antibody combining sites was directed to the T cell receptor (anti-idiotype or anti-allotype) complex structure, while the other antibody combining site was directed to a surface antigen expressed by the targeted tumor cell but not by the CTL.

Mab 19E12 was used as the targeting antibody combining site that was specific for the Thy 1.1 alloantigen, Houston et al., *J. Immunol.*, 125, 837 (1980). The CTL clones G4 and OE4 both expressed Thy 1.2 but not Thy 1.1, and did not immunoreact with (bind to) this Mab. The target cell was S.AKR (H-2$^k$, Thy 1.1).

Two ligand molecules were constructed using the cross-linker SPDP. Those ligand molecules are referred to as hybrid (A), a 19E12-F9A7.3 Mab hybrid, and hybrid (B), a 19E12-F23 Mab hybrid. Both ligand molecules worked efficiently, and specifically as shown in FIG. 9.

Hybrid (A) targeted S.AKR cells for lysis by G4 cytotoxic effector T lymphocytes (FIG. 9b), while hybrid (B) targeted S.AKR cells for lysis by OE4 cytotoxic effector T lymphocytes (FIG. 9d). Neither ligand molecules targeted EL4 (H-2$^b$, Thy 1.2) cells for lysis.

Thus, the above results illustrate that targeting via an antibody combining site is an effective means for lysing target cells. Mixtures of unconjugated Mabs did not permit target lysis under any conditions.

Therapeutic applications of the present invention in generating cytotoxic effector T lymphocytes that bear a Mab-defined receptor determinant from any individual were screened. The anti-allotypic Mab F23.1 reacted with approximately 25 percent of peripheral T cells (both CTL and non-cytolytic T cells), was mitogenic for resting, peripheral T cells from mouse strains that were allotype positive and induced effector CTL that bore the allotypic determinant.

Figure 10:
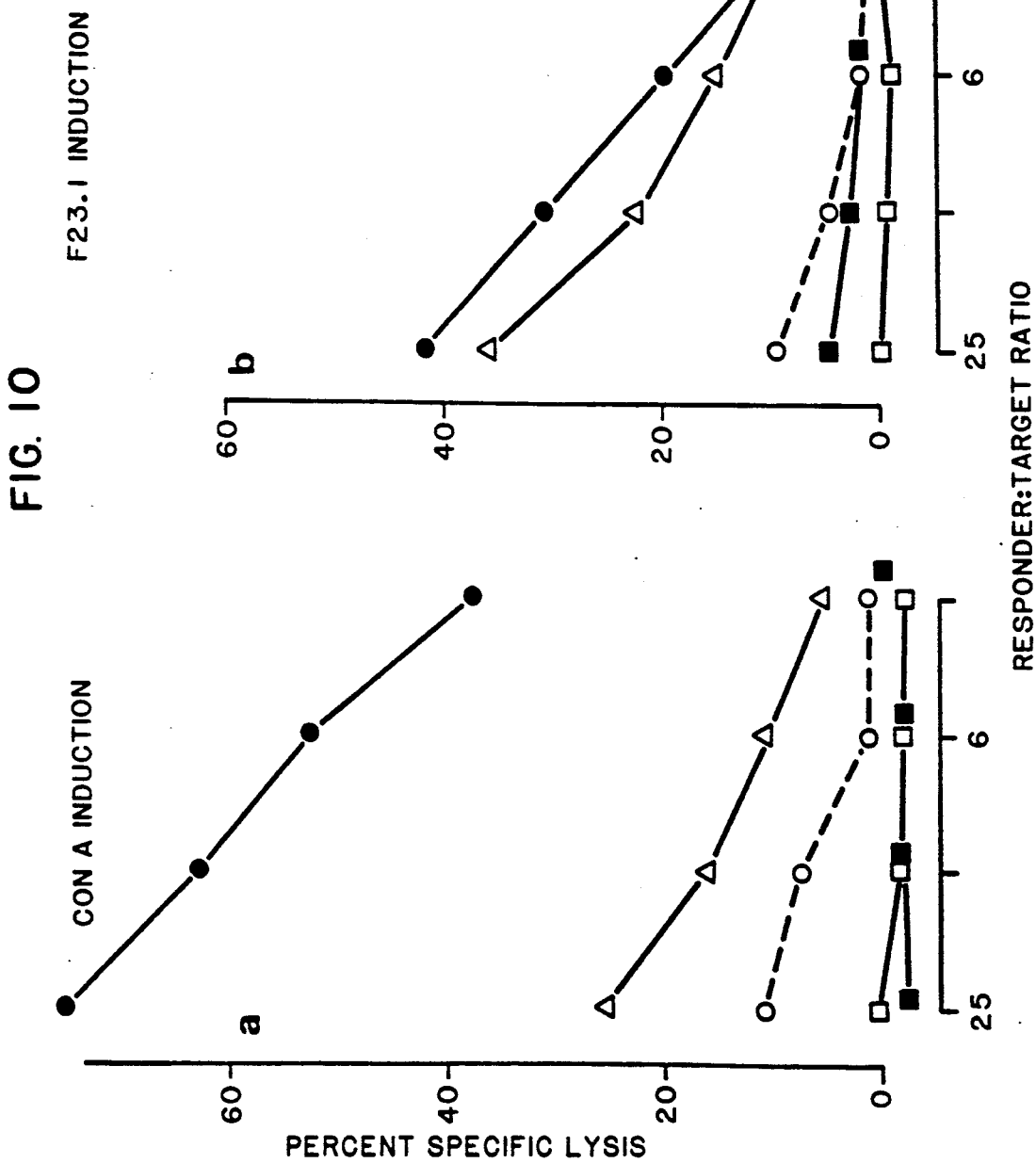
FIG. 10 is a pair of graphs illustrating the cytotoxic effects of Concanavalin A (Con A) induced and Mab F23.1 induced spleen cells revealed on various targets. Spleen cells from normal BALB.B (H-2$^k$) mice were cultured for 4 days at $1 \times 10^6$ cells/ml in RPMI 1640 medium also containing 10 percent fetal calf serum and 10 percent Con A induced rat spleen cell supernatant with 2.5 micrograms/milliliter (ug/ml) Con A (panel a) or with Mab F23.1 coupled to Sepharose beads ($10^3$ beads per ml, panel b). Mab F23.1 cultures also contained 50 mM alpha-methyl-D-mannoside to block the action of residual Con A present in the rat spleen supernatant. Cells were harvested, washed, and serial two-fold dilutions were assayed for lysis of the following $^{51}$Cr-labelled target cells: P815 (○), P815 in the presence of 10 ug/ml phytohemagglutinin (PHA) ), AK-R.A1 (●), AKR.A1 (□), AKR.A1 cells pre-incubated with 19E12 (anti-Thy 1.1)-F23.1 conjugate (△), and AKR.A1 cells pre-incubated with the 19E12-F9A7.3 conjugate ■. AKR.A1 is a T cell lymphoma derived from an AKR/J mouse that expressed H-2$^k$ and Thy 1.1.

FIG. 10 shows the cytotoxic activity of BALB.K (H-2$^k$) spleen cells that had been induce with either (i) the pan-T cell mitogen Con A or (ii) Mab F23.1 coupled to Sepharose beads; both inductions being for a time period of four days in the presence of exogenously supplied IL-2. Con A induced CTL and helper T cells regardless of their antigen specificity. The CTL activity was assayed in an antigen-independent manner by the ability to lyse any target cell coated with an agglutinant such as Con A or PHA according to Bevan et al., *J. Immunol.*, 114, 559 (1975).

FIG. 10a shows that Con-A induced BALB.K cells did not specifically lyse P815 or AKR.A1 (H-2$^k$, Thy 1.1) targets, but did lyse such targets in the presence of PHA. A fraction of the lytic activity revealed by PHA was also measured on AKR.A1 cells targeted by the 19E12-F23 receptor molecules. In the case of Mab F23.1-induced spleen cells (FIG. 10b), PHA plus P815 cells and the receptor molecule targeting AKR.A1 cells revealed approximately equal amounts of lytic activity. The levels of killing correlated well with other data showing that the bulk of Mab F23.1-induced T cells expressed the Mab F23.1 determinant, whereas only about 20 percent of Con A-induced T cells expressed the F23.1 determinant.

As has previously been reported for lectin-induced, lectin-revealed cytotoxicity, Bevan et al., *J. Immunol.*, 114, 559 (1975), all of the Mab induced cytotoxicity was sensitive to treatment with anti-Thy 1.2 antibody plus complement, and was due to T cells, as shown in Table III below:

TABLE III

Mab-Induced Cytolytic Cells Express Thy 1.2*

| Target cells | Con A-induced effectors | | Mab F23.1-induced effectors | |
|---|---|---|---|---|
| | C' treated | anti-Thy-1.2 + C' | C' treated | anti-Thy-1.2 + C' |
| P815 with PHA | 76.5 | 0.4 | 39.8 | −0.6 |
| AKR.A1 with 9E12-F23.1 | 24.2 | −0.8 | 36.7 | −0.9 |

*Spleen cells from normal BALB.K mice were cultured for 4 days in the presence of 2.5 micrograms per milliliter (ug/ml) Con A, or Mab F23.1 covalently coupled to Sepharose beads plus 10 percent supernatant of rat spleen cells that had been cultured with Con A for 24 hours as a source of IL-2. Cultures without Con A also contained 50 mM alpha-methyl-D-mannoside to block the effect of Con A. Cells were harvested and treated with complement (C') alone or with monoclonal anti-Thy-1.2 [Marshak-Rothstein et al., *J. Immunol.*, 122, 2491 (1979)] plus C', and surviving cells were admixed with $^{51}$Cr-labelled target cells, and the admixture maintained for a time period of 4 hours. Targets were P815 cells used in the presence of 10 ug/ml PHA, or AKR.A1 cells that had been incubated with receptor molecules of this invention (19E12-F23.1) for a time period of 20 minutes, and washed. AKR.A1 is a T cell lymphoma cell line from AKR/J mice that express H-2$^k$ and Thy-1.1. Spleen cells cultured with no stimulus had less than 1 percent of the cytotoxic (cytolytic) activity shown here on either target. Assays were performed at a killer:target ratio of 25:1 for the complement (C') treated cells and the equivalent number of surviving cells from the anit-Thy-1.2- treated groups.

III. Materials and Methods

A. Alloantibodies to the Murine T Cell Antigen Receptor

1. Mice

A.TL, BALB.B, BALB/c ByJ, CBA/J, C3H.OH, and DBA/2 mice were obtained from the breeding colony at Scripps Clinic and Research Foundation, La Jolla, California. C57L/J, C57BR/cdJ, C57BL/10nSn, and SJL/J mice were purchased from The Jackson Laboratory, Bar Harbor, Maine.

2. Cell Lines

The cloned CTL lines B10 and G4 were derived from BALB.B (H-2$^b$) mice immunized in vivo and in vitro with BALB/c (H-2$^d$) cells, and were provided by M. Pasternack of The Children's and Medical Services (Infectious Disease Units), Massachusetts General Hospital, Boston, MA. The cell lines are further described in Staerz et al., *Proc. Natl. Acad. Sci. (USA)*, 81, 1799 (1984).

3. Antibodies and Antisera

Monoclonal rat antibody KJ16-133 (Mab KJ16-133) provided by P. Marrack of the National Jewish Hospital, Denver, Colorado, was used as culture supernatant as were murine monoclonal antibodies F23.1 (IgG2a,-Kappa) and F23.2 (IgG1,Kappa). Both were obtained by fusion of P3×63-Ag8.653 myeloma cells (ATCC CRL 1580) with antibody-producing spleen cells from a C57L/J mouse hyperimmunized with BALB.B T cells. The murine monoclonal antibody, F9A7.3 (IgG1,Kappa), that is clonotypic for the cloned CTL line G4, was used in an ascites preparation. The rat monoclonal antibody, Jlld, Bruce et al., *J. Immunol.*, 127, 2496 (1981), was used with complement to remove B cells from peripheral lymphoid populations for the limiting dilution analysis. Rabbit antiserum against rat IgG (RARIG) and fluorescein-coupled goat anti-mouse Ig antibodies (FITC-GAMIG) were purchased from Cappel Laboratories, Cochranville, Pennsylvania. Antiserum against murine IgG was produced in rabbits (RAMIG) following usually used procedures.

4. Immunization

C57L/J mice were immunized intraperitoneally with about $2 \times 10^7$ viable BALB.B T cells suspended in balanced salt solution. The T cells were purified from lymph nodes and spleens of normal mice by fractionation through nylon wool columns as described in Julius et al., *Eur. J. Immunol.*, 3, 645 (1973). Injections were repeated every 10 days. Animals selected for fusion were allowed to rest for 4 weeks before receiving a final immunization of $2 \times 10^7$ BALB.B T cells intravenously 3 days prior to collecting of the antibody-producing cells and fusion.

5. Fusion Protocol

Three days after the final booster immunization, mice were sacrificed, antibody-producing spleen cells were collected, and suspensions of those cells were prepared by standard procedures. Spleen cells cleared of erythrocytes were mixed with P3×63-Ag8.653 myeloma cells in a ratio of about 10:1. After centrifugation, the mixed pellet was suspended in 0.5 ml of polyethylene glycol 1000 present at 33 percent in Dulbecco's Modified Eagle's Medium (DMEM), and was incubated for 2 minutes at 37° C. FollOwing the addition of 4 ml of warm DMEM, the mixture was transferred to Petri dishes containing 5 ml of 36 percent fetal calf serum in DMEM, and was incubated for 24 hours at 37° C.

Thereafter, the fused cells derived from one spleen were distributed into 768 flat-bottomed wells of microtiter plates (Costar, Cambridge, MA) containing HAT medium consisting of 20 percent fetal calf serum in DMEM supplemented with 2 millimolar (mM) glutamine, nonessential amino acids, 1 mM hydroxypyruvate, penicillin at 100 international units per milliliter (IU/ml), streptomycin at 100 ug/ml, gentamycin at 50 ug/ml, 0.1 mM hypoxanthine, 0.16 mM thymidine, 4 micromolar (uM) aminopterin, and 50 uM 2-mercaptoethanol.

Spleen cells from a C57L/J mouse hyperimmunized with BALB.B T cells that produced the antiserum, C3, were fused to the myeloma line P3X63Ag8.653, generally as described above. Two obtained hybridomas were designated F23.1 and F23.2.

6. Cell Surface Labeling and Cell Lysis

Cells were surface radioiodinated by the lactoperoxidase method as described in Staerz et al., *Proc. Natl. Acad. Sci. (USA)*, 81, 1799 (1984), washed extensively, and were recovered by centrifugation. The resulting pellet was lysed at $10^7$ cells/ml in immunoprecipitation buffer consisting of 20 mM $Na_2HPO_4$, 150 mM NaCl, 2 mM EDTA, 2 mM ethylenebis(oxyethylenenitrilo)-tetraacetic acid (EGTA), 8 mM N-ethylmaleimide, aprotinin at 20 IU/ml, ovatrypsin inhibitor at 0.02 milligrams per milliliter (mg/ml), 1 mM phenylmethylsulfonylfluoride, bovine serum albumin at 1 mg/ml, and 1 percent Triton ×100 [polyoxyethylene (9) nonylphenyl ether], at a pH value of 7.6. The lysate was stored on ice for 1 hour then centrifuged at 100,000×g for 30 minutes. Aliquots of the supernatant were used for immunoprecipitation screenings.

7. Immunoprecipitation

Samples of the cell lysates were precleared with Protein A-bearing *Staphylococcus aureus* (Pansorbin, Behring Diagnostics, La Jolla, CA). The precleared lysates were either twice precipitated with antibody and RAMIG or RARIG-coated protein A-Sepharose beads (Protein A-Sepharose CL-4B, Pharmacia, Uppsala, Sweden), or with anti-Ig-coated beads alone. These pre-precipitated lysates were admixed and maintained (incubated) with aliquots of hybridoma supernatants or sera for a time period of 2 hours at 4° C.

The antigen-antibody complexes were harvested by admixture with RAMIG-coated protein-A-Sepharose beads, and maintenance of the admixture for a time period of about 18 hours (overnight), and were extensively washed alternately with wash buffers I and II. Wash buffer I contained 20 mM $Na_2HPO_4$, 2 mM EGTA, 8 mM N-ethylmaleimide, 2 mg/ml bovine serum albumin, 1 percent Triton X100, 0.5 percent deoxycholic acid, 500 mM NaCl and 2 mM EDTA, at a pH value of 7.6. Wash buffer II was identical to wash buffer I with the exception that 120 mM NaCl, 10 mM EDTA and 0.1 percent sodium dodecyl sulfate (SDS) were utilized. Samples were analyzed by SDS-polyacrylamide gel electrophoresis (SDS-PAGE) on a 7.5-15 percent gradient gel according to the procedure of Laemmli, *Nature*, 227, 680 (1970).

8. Immunofluorescence

Murine T cells were purified from lymph nodes on nylon wool as described in Julius et al., *Eur. J. Immunol.*, 3, 645 (1973). The T cells were coated with antibodies against cell surface antigens by admixing the antibodies and cells, and maintenance of the admixture for a time period of 30 minutes on ice or at 37° C. After thorough washing, bound antibodies were detected by admixture of the cells with FITC-GAMIG at room temperature and maintenance of the admixture. The extent of antibody binding to the fixed cells was analysed by a Fluorescence Activated Cell Sorter (FACS IV, Becton-Dickinson, Sunnyvale, CA).

9. Limiting Dilution Analysis

Serial 3-fold dilutions of Mab Jlld and complement-treated peripheral T cells from BALB.B mice were cultured in 24 replicates with $7.5 \times 10^5$ irradiated (2000 rad) stimulator spleen cells of BALB/c origin in round bottomed microtiter plates (Costar 3799, Cambridge, MA) in a total volume of 0.2 ml. Culture medium, RPMI 1640 (M.A. Bioproducts, Walkersville, MD) containing penicillin, streptomycin, L-glutamine, $3 \times 10^{-5}$M 2-mercaptoethanol and 5 percent fetal calf serum was supplemented with 50 mM alpha methyl-D-mannoside and 5 percent Con A supernatant harvested from Lewis rat spleen cells cultured for 24 hours at $5 \times 10^6$ cells/ml with 5.0 ug/ml Con A. These plates were incubated for 7 days and assayed for cytolytic activity against $^{51}Cr$ labelled EL4 ($H-2^b$) targets.

A culture was considered positive when the released $^{51}Cr$ exceeded the spontaneous release from target cells assayed on activators alone by at least three standard deviations. The percentage of negative cultures was plotted against the number of responder cells per well according to the procedure of Miller, "Cloning Analysis by Limiting Dilution", in *Isolation, Characterization and Utilization of T Lymphocyte Clones*, Fathman et al., eds., Academic Press, New York, p. 220 (1982).

Best fit lines were calculated by a linear regression analysis using the function:

$$-\ln F_o = a + bx$$

where $F_o$ was the fraction of negative cultures, a the y-axis intercept, b the slope of the fitted line, and the number of responding cells per well. Correlation coefficient ($r^2$) and a were indicated in each study as a measure of fit. Precursor frequencies were defined by $-\ln F_o = 1$, or $F_o = 0.37$. The results are shown in Table III hereinbefore.

B. Targeting Sites for Lysis By Cytotoxic Effector T Lymphocytes

1. Monoclonal Antibodies

Monoclonal antibodies F23.1 and F23.2 were secreted by hybridomas of the same respective designations that were deposited with the American Type Culture Collection, Rockville, MD on July 10, 1985, and assigned the designations ATCC HB 8867 and ATCC HB 8868, respectively. All hybridomas and their monoclonal antibodies described herein by an "ATCC" designation are on deposit with the American Type Culture Collection.

The deposits were made in compliance with the Budapest Treaty requirements that the duration of the deposit should be for 30 years from the date of deposit or for 5 years after the last request for the deposit at the depository or for the enforceable life of a U.S. patent that matures from this application, whichever is longer. The hybridomas will be replenished should they become non-viable at the depository.

The hybridomas and resultant monoclonal antibodies F23.1 and F23.2 were prepared and characterized by methods well known in the art as described before in Section III.A.4.

Three days after the final booster immunization, mice were sacrificed and antibody producing splenocytes were harvested and cleared of erythocytes by standard procedures as described before in Section III.A.5.

Monoclonal antibodies F23.1 and F23.2 were subsequently further characterized, using the immunoprecipitation assay also described hereinafter, as being immunospecific for an allotypic determinant on the T lymphocyte antigen receptor of the cytotoxic T lymphocyte (CTL) clonal cell line OE4.

Monoclonal antibody F9A7.3 was secreted by a hybridoma of the same designation that was deposited on July 10, 1985 in the ATCC, Rockville, MD and was assigned the designation ATCC HB 8866.

Hybridoma F9A7.3 was produced essentially as described in Staerz et al., *Proc. Natl. Acad. Sci. (USA)*, 81, 1799 (1984), which description is herein incorporated by reference. Briefly, antibody-producing spleen cells from a BALB/cByJ mouse hyperimmunized with G4 cells (a mouse T cell line more completely described hereinafter) were fused to the mouse myeloma line P3×63-Ag8.653.

Antibodies secreted by hybrids derived from the above fusion were screened for, inter alia, their ability to inhibit CTL-mediated (i.e., G4-mediated) lysis of labeled P815 target cells, Staerz et al., *Proc. Natl. Acad. Sci (USA)*, 81, 1799 (1984). Monoclonal antibody F9A7.3 was found to inhibit G4-mediated lysis. In addition, Mab F9A7.3 was further characterized as being immunospecific for an idiotypic determinant expressed on the T cell antigen receptor of G4 cells.

Monoclonal antibody 20-8-4S was obtained from ascites fluid provided by Keiko Ozato and David Sachs of the Transplantation Biology Section, Immunology Branch, National Cancer Institute, National Institutes of Health, Bethesda, MD 20205. The hybridoma that produced 20-8-4S is available from the ATCC and designated as ATCC HB 11. Its production and characterization were described in Ozato et al., *J. Immunol.*, 126, 317 (1981), which description is herein incorporated by reference. Briefly, 20-8-4S immunoreacted with mouse major histocompatibility complex (MHC) products of the H-$2^b$ halotype and did not immunoreact with either an allotypic or idiotypic determinant on the T cell antigen receptor.

Monoclonal antibody 19E12 was produced from a hybridoma provided by Ian Trowbridge of the Salk Institute, La Jolla, CA 92037. The production and characterization of Mab 19E12 was reported in Houston et al., *J. Immunol.* 125, 837 (1980). Monoclonal antibody 19E12 immunoreacted with the Thy-1.1 alloantigen expressed on some T lymphocytes, e.g., SAKR cells. Monoclonal antibodies of similar Thy-1.1 immunospecificity are also available commercially from New England Nuclear, Boston, MA.

As is well known in the art, monoclonal antibodies secreted by hybridomas may be recovered from the tissue culture supernatant in which the hybridoma is cultured or in generally more concentrated form from ascites fluids of hybridoma-bearing host mammals. In the present studies, both tissue culture supernatant- and ascites-derived antibodies were used, the choice of source for a given study being mainly a function of desired concentration.

Monoclonal antibodies used in the CTL-targeting studies described herein were first dialyzed, and were then purified from ascites fluid by affinity chromatography using a Protein A-Sepharose CL-4B (Pharmacia) column (20cm ×1.2cm) equilibrated with 0.14 M $Na_2HPO_4$ and 0.12 M NaCl at a pH value of 8.7. The dialyzed ascites were loaded onto the column at a rate of 20 ml/hr. The column was subsequently washed with 0.14 M $Na_2HPO_4$, at a pH value of 8.7, at 40 ml/min until no protein was detectable by spectrophotometric adsorbance at 280 nanometers (nm).

The purified monoclonal antibody was then eluted with 0.1 M sodium citrate at a pH value of 3.0 at 40 ml/min. The eluted antibodies were transferred to phosphate-buffered saline (PBS), at a pH value of 7.4, by dialysis.

2. Cell Lines

The present screening used the mouse lymphoid cell lines.-G4 -and OE4 as sources of inducible T lymphocytes. Cell line G4 was provided by Mark S. Pasternack of The Children's and Medical Services (Infectious Disease Units), Massachusetts General Hospital, Boston, MA. The inducible cytolytic activity of G4 was reported in Staerz et al., *Proc. Natl. Acad. Sci. (USA)*, 81, 1799 (1984). Cell line OE4 was provided by Osami Kanagawa of Lilly Research Laboratories, 3252 Holiday Court, Suite 101, La Jolla, CA. Cell lines AKR.A1 and S.AKR were obtained from Dr. Robert Hyman of the Salk Institute, San Diego, California. Cell lines EL4 and P815 were obtained from Dr. Melvin Cohen of the Salk Institute, San Diego, California, and are also available from the American Type Culture Collection Rockville, Maryland, under the designations ATCC TIB 39 and ATCC TIB 64, respectively.

3. Coupling of Monoclonal Antibodies to Target Cell Surface Proteins

Initially, it was important to determine whether or not anti-CTL monoclonal antibodies could focus activity against otherwise non-targeted cells. This was accomplished by separately chemically (covalently) coupling monoclonal antibodies F23.1, F9A7.3 and 20-8-4S to nonspecific proteins on the surface of viable target (S.AKR) cells. The antibody coated target cells were then exposed to CTL's.

Anti-CTL monoclonal antibodies were coupled to the target cell surface using the heterobifunctional protein cross-linker N-succinimidyl -3-(2-pyridyldithio)-propionate (SPDP). Briefly, 2-pyridyl-disulphide residues were admixed and reacted with the monoclonal antibodies in amounts of 5 ml of antibody (2 mg/ml in PBS at a pH of 7.4) and 43 microliters of SPDP (5 mM in absolute ethanol). The ratio of SPDP to antibody, about 3 to 1, resulted in the introduction of about two or three 2-pyridyl disulphide residues per antibody. The admixtures were subsequently maintained at 20° C. under nitrogen for 30 minutes with intermittent agitation.

The reacted admixture was run over a Sephadex G25 column (30 cm × 1.2 cm) using PBS (pH 7.4) at a flow rate of about 60 ml/min at 20° C. to separate the activated antibody from excess SPDP and reaction by-products. The protein-containing fractions were collected and pooled.

Proteins on the surface of S.AKR (target) cells were reduced so as to become coupling partners for the above-obtained activated antibodies. About $10 \times 10^6$ viable target cells in 1 ml of RPMI 1640 containing 5 percent fetal calf serum were admixed with 80 microliters of 10 mM dithiothreitol, a cystine disulfide bond reducing agent. The admixture was then maintained at either 20° C. or 37° C. for 30 minutes. The resulting reduced target cells were washed twice by centrifugation, pelleting, and resuspension in 1 ml of RPMI 1640 with 5 percent fetal calf serum.

The activated antibodies were then coupled to the reduced cell surface proteins by admixing 2 ml of cells in PBS at $2 \times 10^6$ cells/ml and 1 ml of activated antibodies in PBS at 0.25 mg/ml in bovine serum albumin-coated Petri dishes. The admixture was maintained 30 minutes at 20° C. with intermittent swirling. The resulting anti-CTL antibody-coated target cells were then washed twice as described above.

4. Construction of Heteroantibodies

Exemplary heteroantibodies (hybrid antibodies) were constructed in vitro using the SPDP crosslinking method described above.

Anti-CTL monoclonal antibodies F23.1 and F9A7.3 were separately coupled to the anti-target monoclonal antibody 19E12. All three antibodies were purified from ascites fluids as described hereinbefore. In separate reactions, all three antibodies had 2-pyridyl disulphide residues introduced as described above. However, to separate the activated antibodies from excess SPDP and reaction by-products, the reaction admixtures were eluted from the Sephadex G25 column using a 0.1 M sodium acetate, 0.1 M NaCl buffer at a pH value of 4.5. The pooled antibody-containing fractions contained antibody at a protein concentration of about 0.7 mg/ml.

After activation, the 2-pyridyl disulphide groups on the anti-target (19E12) antibody were reduced so as to become a coupling partner for either of Mabs F23.1 or F9A7.3. This was accomplished by admixing dithiothreitol to a final concentration of 50 mM with Mab 19E12. The admixture was maintained at a temperature of 20° C. for 20 minutes under nitrogen with intermittent agitation. Subsequently, the reduced antibody was chromatographically separated from the reducing agent and reaction by-products using Sephadex G25 in a 30 cm × 1.2 cm column at 20° C. and PBS elution buffer, at a pH value of 7.4, at 60 ml/minute. The protein (antibody) containing fractions were pooled.

Approximately equal amounts of antibody protein were admixed; i.e., Mab F23.1 plus Mab 19E12, or Mab F9A7.3 plus Mab 19E12 to crosslink either F23.1 or F9A7.3 activated monoclonal antibodies with reduced 19E12 antibodies. The admixtures were maintained at a temperature of 20° C. under nitrogen for about 2 hours, and then dialyzed against PBS at a pH value of 7.4.

An alternative method of constructing the hybrid antibodies of the present invention is that described in Brennan et al., *Science*, 229, 81 (1985). Briefly, two different F(ab)'$_2$ fragments are reduced with 2-mercaptoethylamine in the presence of sodium arsenite. The fragments are then converted to thionitrobenzoate (TNB) derivatives by reaction with 5,5'-dithiobis(2-nitrobenzoic acid) (Ellman's reagent). One of the Fab'-TNB derivatives is then reconverted to the Fab'-thiol by reduction with 2-mercaptoethylamine and is mixed with an equimolar amount of the other Fab'-TNB derivative to form the hybrid dimer.

Further alternative methods of preparing the hybrid antibodies are described in U.S. Pat. Nos. 4,444,878 and 4,355,023, the teachings of which are incorporated herein by reference.

5. Binding Monoclonal Antibodies to Sepharose 4B

Precursor T lymphocytes were induced to proliferate and differentiate into effector cytotoxic T lymphocytes by activation with anti-T cell receptor antibodies (F23.1 or F9A7.3) bound to a solid support. Ascites purified Mab F23.1 and Mab F9A7.3 were transferred into 0.2 M NaHCO$_3$, 0.5 M NaCl, buffer (pH 8.7) by dialysis, and diluted to a concentration of about 2 mg/ml. CNBr activated Sepharose 4B beads (Pharmacia) were prepared by first swelling the beads in 10 ml of 0.001 M HCl per gram of dry beads, and then washing the swollen beads with 10 ml of 0.2 M NaHCO$_3$, 0.5M NaCl buffer (pH 8.7) for every gram of dry beads.

Antibodies were coupled to activated Sepharose beads by admixing beads and antibody at a ratio of 2.7 mg antibody protein to 1 ml of swollen, washed beads. After admixture, the volume of the reaction solution was adjusted until the bead volume was about one third of the total reaction volume by adding 0.2 M NaHCO$_3$, and 0.5 M NaCl buffer at a pH value of 8.7. The reaction admixture was then maintained with constant agitation at a temperature of 20° C. for 2 hours.

Subsequently, uncoupled antibody was removed by centrifuging and pelleting the beads, and removing the supernatant. Any residual active sites on the beads were then blocked by resuspending the beads in 0.2 M glycine, 0.2 M NaHCO3, and 0.5 M NaCl buffer at a pH value of 8.3, and maintaining the admixture with constant agitation for a time period of 30 minutes at a temperature of 20° C. or for a time period of 16 hours at a temperature of 4° C. The antibody-coupled beads were then washed six times with either 0.2 M NaHCO$_3$, 0.5 M NaCl buffer, at a pH value of 8.7, or 0.1 M sodium acetate buffer, at a pH value of 4.5. The antibody-Sepharose 4 B beads were stored in PBS containing 1 percent Triton $\times 100$ at a temperature of 4° C.

6. Targeting Assay

The purpose of the targeting assay described herein was to determine whether or not anti-T cell receptor antibodies attached to target cells could immunologically react with effector T cells so as to induce their cytolytic activity and focus it upon the target cells. In some assays, the anti-T cell receptor monoclonal antibodies F23.1 or F9A7.3 were attached to the target cells by covalent coupling to target cell surface proteins as described hereinabove. In other assays, ligand molecules containing Mab F23.1 or Mab F9A7.3 coupled to the anti-target cell antibody 19E12 were constructed and attached to the target cells by immunological binding to form an immunoreactant. In either case, the targeting assays varied only as to the method of coating target cells with anti-T cell receptor antibody and type of target cell.

The target cells were first labelled by incubating about $10 \times 10^6$ cells in 1 ml of RPMI 1640 medium supplemented with 5 percent FCS, 5 mM HEPES, 100 IU/ml penicillin. 100 ug/ml streptomycin, 2 mM glutamine and 50 ug/ml gentamycin, and containing 50 mCi sodium chromate ($^{51}$Cr)for a time period of 60 minutes at a temperature of 37° C. Once labelled, the target cells were subsequently either 1) covalently conjugated with Mab F23.1 or Mab F9A7.3 as described above; 2) immunologically coated with receptor molecules; 3) treated with PHA at a concentration of 10 ug/ml; or 4) left otherwise unmodified as a control.

To coat the labelled target cells with ligand molecules of this invention, about $1 \times 10^6$ target cells in 1 ml of the supplemented RPMI 1640 medium described above were admixed with 200 microliters of 0.2 mg/ml ligand molecule solution, maintained for a time period of 20 minutes at a temperature of 20° C., and then washed twice in RPMI 1640 medium supplemented as above.

Aliquots of appropriately prepared target cells were placed into Costar 96 well round-bottomed microliter plates at $1 \times 10^4$ cells per well. Effector cells were then admixed with the target cells at effector to target ratios of about 25:1 through about 1.25:1; i.e., about $2.5 \times 10^5$ through about $1.25 \times 10^4$ effector cells per well. The final volume per well was 0.2 ml of supplemented RPMI 1640 medium and cells.

After admixture, the plates were spun for one minute at 700 rpm in a centrifuge, and were then maintained for a time period of 4.5 hours at a temperature of 37° C., in 6 percent $CO_2$, atmospheric $O_2$ and 100 percent relative humidity. The plates were then centrifuged for a time period of 5 minutes at 2000 rpm, and supernatant aliquots collected and counted in a Gamma Trac 1191 sold by Tm Analytic, Elk Grove Village, IL.

The total possible number of counts released upon complete lysis of $1 \times 10^4$ target cells was determined for each study by including as a control $1 \times 10^4$ labeled target cells maintained in 0.2 percent Triton $\times 100$ instead of RPMI 1640 medium. The number of counts released due to spontaneous lysis during each study was determined by incubating $1 \times 10^4$ labeled target cells in RPMI 1640 medium.

The Government has certain rights in this invention pursuant to Grant No. CA-25803 awarded by the United States Public Health Service.

The foregoing is intended as illustrative of the present invention but not limiting. Numerous variations and modifications may be effected without departing from the true spirit and scope of the invention.

What is claimed is:

1. A hybrid ligand molecule comprising one antibody combining site that binds to a T cell receptor complex structure and is capable of activating cytotoxic effector T lymphocytes linked to a second target cell-specific antibody combining site.

2. The hybrid ligand molecule of claim 1 wherein said antibody combining site that binds to a T cell receptor complex structure is directed to a T cell antigen receptor on the surface of T lymphocytes.

3. The hybrid ligand molecule of claim 1 wherein said antibody combining site that binds to a T cell receptor complex structure is directed to a T3 complex on the surface of T lymphocytes.

4. The hybrid ligand molecule of claim 1 wherein said antibody combining site that binds to a T cell receptor compelx structure is directed to the major histocompatibility complex on the surface of T lymphocytes.

5. The hybrid ligand molecule of claim 1 wherein said target cell-specific antibody is an antibody combining site that binds to a target cell-specific surface antigen.

6. The hybrid ligand molecule of claim 5 wherein said antibody combining site that binds to a target cell-specific antigen is directed to a viral protein expressed on the surface of said target cell.

7. The hybrid ligand molecule of claim 5 wherein said antibody combining site that binds to a target cell-specific antigen is directed to an oncogene protein expressed onthe surface of said target cell.

8. The hybrid ligand molecule of claim 1 wherein said target cell is a tumor cell.

9. A hybrid ligand molecule comprising a plurality of different, linked antibody combining sites, one of said combining sites binding to a T cell receptor complex structure, and another of said combinng site binding to a target cell-specific antigen.

10. A composition including hybrid ligand molecules dispersed in a physiologically tolerable diluent, said hybrid lignad molecules comprising a plurality of different, linked antibody combining sites, one of said combining sites binding to a T cell receptor complex structure and another of said combining sites binding to a target cell-specific antigen, said composition, when contacted in an effective amount in vitro with target cells in the presence of an exogenously supplied source of cytotoxic effector T lymphocytes, inducing lysis of the target cells by said cytotoxic effector T lymphocytes.

11. A method of killing tumor cells including the steps of:

(a) providing a composition containing a unit dose of hybrid ligand molecules dispersed in a physiologically tolerable diluent, said ligand molecules comprising a first and a second antibody combining site linked together, said first antibody combining site binidng to a T cell receptor complex structure and said second antibody combining site binding to a tumor cell-specific antigen, said composition inducing lysis of said tumor cell by cytotoxic effector T lymphocytes that react with cells that bear said antigen;

(b) contacting tumor cells that bear said specific antigen with said composition in the presence of a source of cytotoxic effector T lymphocytes whose production is activated by said first antibody combining site, said composition being present in an amount sufficient to effect binding to said cytotoxic effector T lymphocytes and to said tumor cells; and (c) maintaining said contact for a time period sufficient (i) for said second antibody combining site to bind to said tumor cell-specific antigen and (ii) for said first antibody combining site to bind to and activate production of cytotoxic effector T lymphocytes, said produced cytotoxic effector T lymphocytes cytotoxically reacting with said specific antigen-bearing tumor cells.

12. The method of claim 11 wherein said contacting occurs in an in vitro tumor cell culture and said source is supplied exogenously to said cell culture.

13. The method of claim 12 including the further steps of periodically repeating steps (b) and (c) until substantially all of said tumor cells have been killed.

* * * * *